(12) United States Patent
Krause et al.

(10) Patent No.: US 10,472,303 B2
(45) Date of Patent: Nov. 12, 2019

(54) ALKANE ACTIVATION WITH SINGLE AND BI-METALLIC CATALYSTS

(71) Applicant: UCHICAGO ARGONNE, LLC, Chicago, IL (US)

(72) Inventors: Theodore R. Krause, Naperville, IL (US); Adam S. Hock, Chicago, IL (US); Guanghui Zhang, Naperville, IL (US); Yunjie Xu, Chicago, IL (US)

(73) Assignees: UChicago Argonne, LLC, Chicago, IL (US); Illinois Institute of Technology, Chicago, IL (US)

( * ) Notice: Subject to any disclaimer, the term of this patent is extended or adjusted under 35 U.S.C. 154(b) by 0 days.

(21) Appl. No.: 15/691,666

(22) Filed: Aug. 30, 2017

(65) Prior Publication Data

US 2019/0062235 A1 Feb. 28, 2019

(51) Int. Cl.

| | |
|---|---|
| *B01J 21/08* | (2006.01) |
| *B01J 23/00* | (2006.01) |
| *B01J 23/10* | (2006.01) |
| *B01J 23/28* | (2006.01) |
| *B01J 23/46* | (2006.01) |
| *B01J 23/62* | (2006.01) |
| *B01J 23/75* | (2006.01) |

(Continued)

(52) U.S. Cl.
CPC ............ *C07C 2/76* (2013.01); *B01J 23/002* (2013.01); *B01J 23/10* (2013.01); *B01J 23/28* (2013.01); *B01J 23/42* (2013.01); *B01J 23/62* (2013.01); *B01J 23/6525* (2013.01); *B01J 23/6527* (2013.01); *B01J 23/6567* (2013.01); *B01J 23/75* (2013.01); *B01J 23/862* (2013.01); *B01J 23/8913* (2013.01); *B01J 35/023* (2013.01); *B01J 37/088* (2013.01); *B01J 37/18* (2013.01); *B01J 21/08* (2013.01); *B01J 23/462* (2013.01); *B01J 23/468* (2013.01); *B01J 2523/00* (2013.01); *C07C 2521/08* (2013.01); *C07C 2523/10* (2013.01); *C07C 2523/28* (2013.01); *C07C 2523/46* (2013.01); *C07C 2523/62* (2013.01); *C07C 2523/656* (2013.01); *C07C 2523/75* (2013.01); *C07C 2523/86* (2013.01); *C07C 2523/89* (2013.01)

(58) Field of Classification Search
CPC . B01J 21/08; B01J 23/002; B01J 23/10; B01J 23/28; B01J 23/462; B01J 23/62; B01J 23/6567; B01J 23/75; B01J 23/862; B01J 23/8913

See application file for complete search history.

(56) References Cited

U.S. PATENT DOCUMENTS

| | | | | |
|---|---|---|---|---|
| 4,134,852 A | * | 1/1979 | Volin | B01J 23/002 423/213.5 |
| 4,997,725 A | * | 3/1991 | Pujare | H01M 4/9016 429/482 |

(Continued)

OTHER PUBLICATIONS

Bhasin, M., et al., "Dehydrogenation and oxydehydrogenation of paraffins and olefins," Appl. Cat. A, 2001, V221, pp. 397-419.

(Continued)

*Primary Examiner* — Cam N. Nguyen
(74) *Attorney, Agent, or Firm* — Foley & Lardner LLP

(57) ABSTRACT

Methods, compositions, and articles of manufacture for alkane activation with single- or bi-metallic catalysts on crystalline mixed oxide supports.

11 Claims, 29 Drawing Sheets

(51) Int. Cl.
  *B01J 23/86* (2006.01)
  *B01J 23/89* (2006.01)
  *C07C 2/76* (2006.01)
  *B01J 23/656* (2006.01)
  *B01J 37/08* (2006.01)
  *B01J 37/18* (2006.01)
  *B01J 23/42* (2006.01)
  *B01J 23/652* (2006.01)
  *B01J 35/02* (2006.01)

(56) References Cited

U.S. PATENT DOCUMENTS

| | | | | | |
|---|---|---|---|---|---|
| 7,300,561 | B2 * | 11/2007 | Chaput | ................ | B01D 53/228 204/295 |
| 7,608,744 | B1 * | 10/2009 | Johnston | ................ | C07C 29/149 568/885 |
| 8,450,535 | B2 * | 5/2013 | Johnston | ................ | C07C 29/149 568/861 |
| 8,487,143 | B2 * | 7/2013 | Johnston | ................ | C07C 29/149 568/885 |
| 8,669,400 | B2 * | 3/2014 | Johnston | ................. | B01J 21/08 502/185 |
| 8,853,122 | B2 * | 10/2014 | Johnston | ................ | C07C 29/149 502/327 |
| 9,649,596 | B2 * | 5/2017 | Chang | ................ | B01D 53/9418 |
| 2003/0024389 | A1 * | 2/2003 | Flippo | ................ | B01D 53/0431 95/92 |
| 2008/0081223 | A1 * | 4/2008 | Yasumoto | ............. | C04B 41/009 429/532 |
| 2010/0029995 | A1 * | 2/2010 | Johnston | .................. | B01J 21/08 568/840 |
| 2011/0306806 | A1 * | 12/2011 | Johnston | ................ | C07C 29/149 568/885 |

OTHER PUBLICATIONS

Cavani, F., et al., "Oxidative dehydrogenation of ethane and propane: How far from commercial implementation?", Cat. Tod., 2007, V127, pp. 113-131.

Liu, Y., et al., "Oxidative dehydrogenation of ethane over $Na_2WO_4$—$Mn/SiO_2$ catalyst using oxygen and carbon dioxide as oxidants," Stud. Surf. Sci., Catal. 1998, V119, pp. 593-597.

Ren, T., et al., "Olefins from Conventional and Heavy Feedstocks: Energy in Steam Cracking and Alternative Processes," Energy, 2006, V31, pp. 425-451.

* cited by examiner

ALKANE ACTIVATION WITH SINGLE AND BI-METALLIC CATALYSTS

STATEMENT OF GOVERNMENT INTEREST

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

TECHNICAL FIELD

The present disclosure relates generally to methods for catalyst formation and alkane conversion.

BACKGROUND

As global demand on hydrocarbon reserves has continued to increase, more efficient utilization of petroleum and gas reserves has become an important complementary strategy to the development and deployment of sustainable energy generation.

In particular, alkene (olefin) production is critical for the polymer and chemical industries and is widely utilized as intermediates in the production of transportation fuels. Current olefin production is generally accomplished by thermal cracking of alkanes at high temperatures, to the olefin and hydrogen, and catalytic dehydrogenation with Pt nanoparticle or Cr oxide catalyst technologies at temperatures above about 600° C. where equilibrium favors high alkane yields. For alkanes with three or more carbons, thermal cracking results in mixtures of C—C and C—H cracked products. Propane, for example, produces propylene, ethylene, hydrogen, and methane. Because of the low olefin yields by thermal cracking for C3 and higher hydrocarbons, catalytic conversion processes are often favored. While propylene selectivity is higher for catalytic dehydrogenation of propane than thermal cracking, increasing the propylene selectivity, i.e., reducing the C—C cleavage reaction in favor of the dehydrogenation, remains an important catalytic goal that increases the overall process efficiency by requiring less separation of the products. With catalytic dehydrogenation, there is also deposition of carbon ("coke") on the catalyst surface leading to rapid loss of activity, often in a few hours, thus requiring frequent regeneration and expensive process designs. As a result, improved catalytic materials with higher selectivity, rate, and lowered coke production is an important goal to improve alkene production.

Natural gas production and its reserves in the United States provide a valuable natural resource for energy security. The domestic production of natural gas has increased by approximately one trillion cubic feet per year over the past decade due primarily to recovery from oil shale wells. Recent methods for harvesting natural gas from shale gas deposits decouple natural gas production and cost from those of petroleum. A wide variety of approaches to methane coupling have failed to yield commercializable technology despite intense interest over essentially the whole history of catalysis research. The problems are well-documented and understood, with the principal problem being the necessity of high temperatures for favorable thermodynamics and the kinetic instability of reaction products relative to methane. Heat management is a problem, as dehydrogenation endothermic need efficient means to provide heat—basis for reactor choice. Further, conversion equilibrium is limited, which can require altering pressure or temperature to try to drive conversion. Further, even for catalysts that exhibit acceptable performance initially, catalysts experience high coking levels. This is exacerbated when temperatures are increased to increase conversion, as coking and side reactions (such as cracking and coke formation) increase.

Of particular interest is the Fischer-Tropsch (FT) process, an indirect methane conversion route, which first converts methane to syngas followed by FT synthesis to produce gasoline and diesel. As an alternative to the indirect conversion route, methane can be converted to a liquid fuel by a number of reaction processes including (a) non-oxidative coupling of methane (NOCM) to produce ethylene followed by an oligomerization process to yield aromatics or longer chain linear alkanes/alkenes; (b) oxidative coupling of methane (OCM) in which methane is reacted with a sub-stoichiometric amount of oxygen to produce ethane or ethylene as the primary products, and CO2 and H2O as secondary products, which can also be coupled with an oligomerization process; and (c) selective oxidation to produce methanol followed by a process such as the Mobil "methanol-to-gasoline" process. Conceptually, NOCM should have an economic advantage over OCM or selective oxidation since it does not require the use of expensive oxygen. However, to date, no NOCM process has progressed to a commercial stage. Despite these challenges, methane activation remains an attractive problem.

SUMMARY

Embodiments described herein relate generally to a catalytic article of manufacture comprising: a support comprising either a perovskite having the composition of $La_xSr_{1-x}Cr_yFe_{1-y}O_3$ where x is greater than 0 and less than 1, y is 0.3 to 0.7; and a metallic catalyst selected from the group consisting of metallic and bi-metallic catalysts.

Other embodiments relate to a catalytic article of manufacture comprising a support having amorphous $SiO_2$ and further comprising a bi-metallic catalyst deposited on the support.

Other embodiments relate to a method for non-oxidative coupling of methane comprising: synthesizing a bi-metallic on a $SiO_2$ support to form a bimetallic catalyst and converting methane to ethylene with an initial conversion of 8%.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 2A shows fresh catalysts turn over frequency (TOF) for select $Pt_xRe_x$ catalysts; FIG. 2B shows regenerated catalyst TOF; FIG. 2C shows propene selectivity for select $Pt_xRe_x$ catalysts; FIG. 2D shows regenerated catalyst propene selectivity.

FIG. 3A shows fresh catalysts turn over frequency (TOF) for select $Pt_xCo_x$ catalysts; FIG. 3B shows propene selectivity for select $Pt_xCo_x$ catalysts.

FIG. 5A shows fresh catalysts turn over frequency (TOF) for select $Pt_xGa_y$ catalysts; FIG. 5B shows propene selectivity for select $Pt_xGa_y$ catalysts.

FIG. 6A shows fresh catalysts turn over frequency (TOF) for select $Pt_xGa_y$ catalyst loading; FIG. 6B shows propene selectivity for select fresh $Pt_xGa_y$ catalyst loading; FIG. 6C shows fresh catalysts turn over frequency (TOF) for select regenerated $Pt_xGa_y$ catalyst loading; FIG. 6D shows propene selectivity for select regenerated $Pt_xGa_y$ catalyst loading. FIG. 6E shows TOF for select embodiments. FIG. 6F shows propane dehydrogenation selectivity for select embodiments. $Pt_xGa_y$ is utilized as a selective dehydrogenation material, but any such selective material could be utilized.

FIG. 11A shows thermodynamic ratio of products for $CH_4$ conversion to $C_2$ and $C_3$ products (HSC); FIG. 11B shows product distribution for Hock group catalyst in a pure $CH_4$ feed (equilibrium conversion).

FIG. 18A is a plot of conversion; FIG. 18B is a plot for selectivity. FIG. 18C is a plot of conversion; FIG. 18D is a plot for selectivity.

Figure 1:
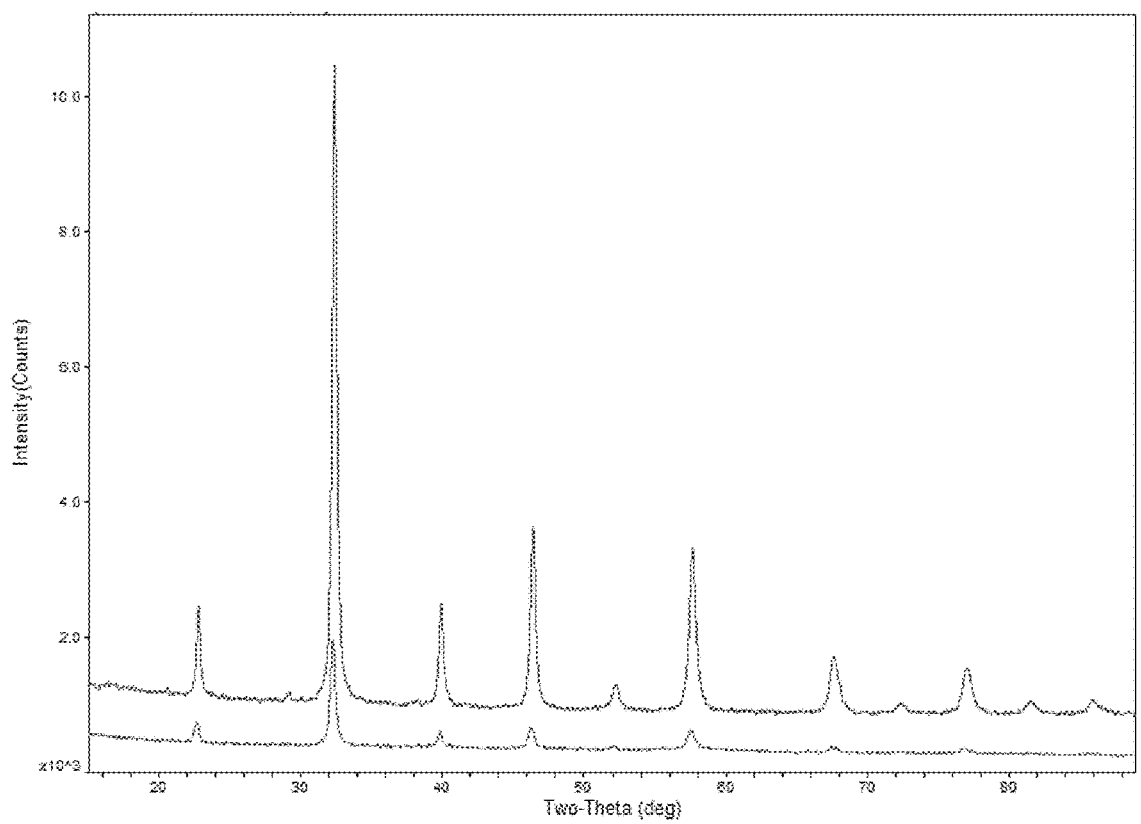
FIG. 1 shows XRD patterns of LSCF (top line) and Ce-LSCF (bottom line).
Figure 2A:
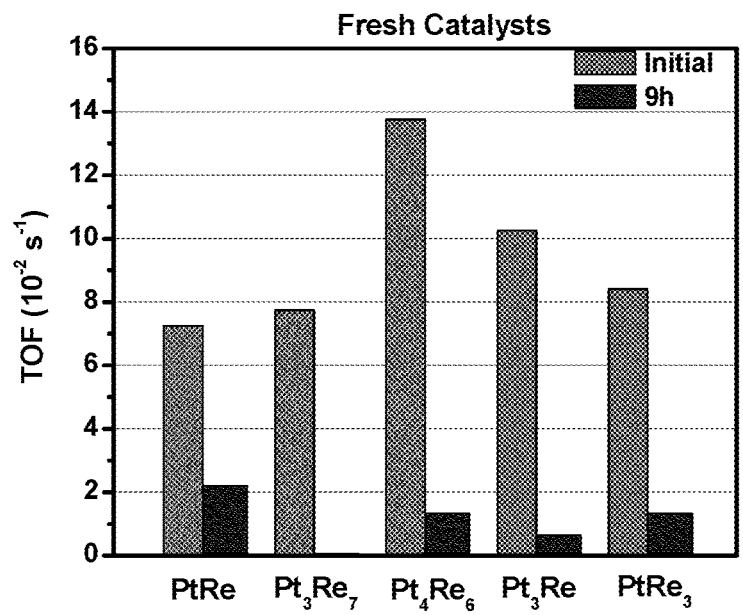
FIGS. 2A-2D show Propane dehydrogenation of $Pt_xRe_y$/LSCF catalysts with various metal ratios (Pt 0.1 wt %).
Figure 2B:
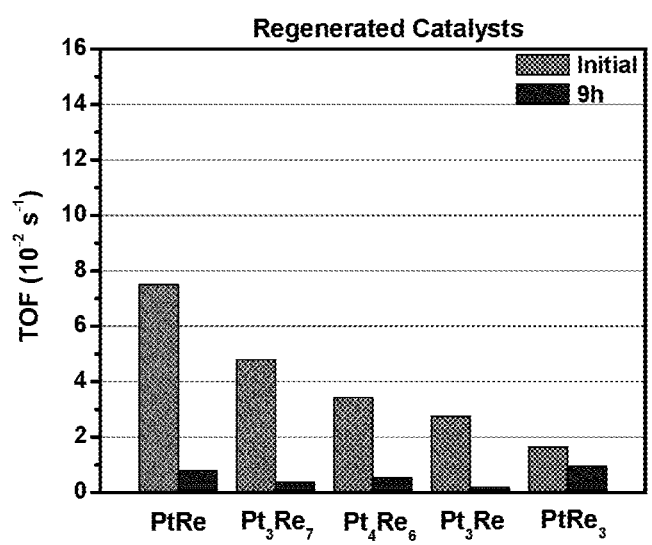
Figure 2C:
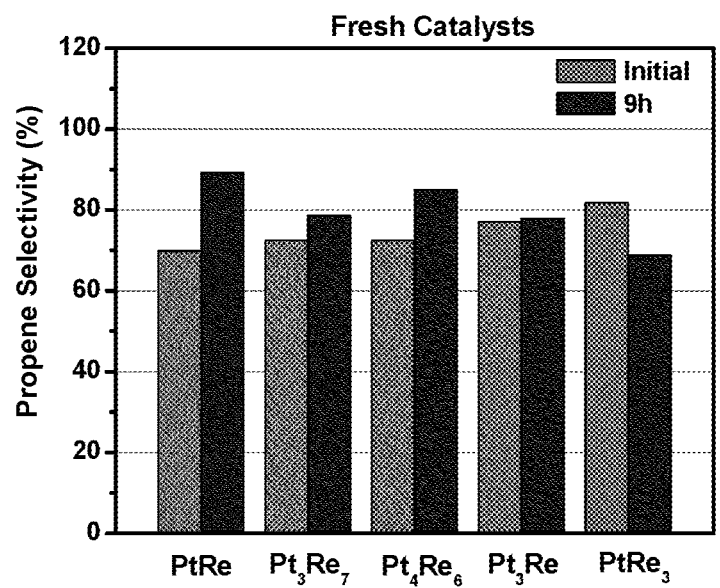
Figure 2D:
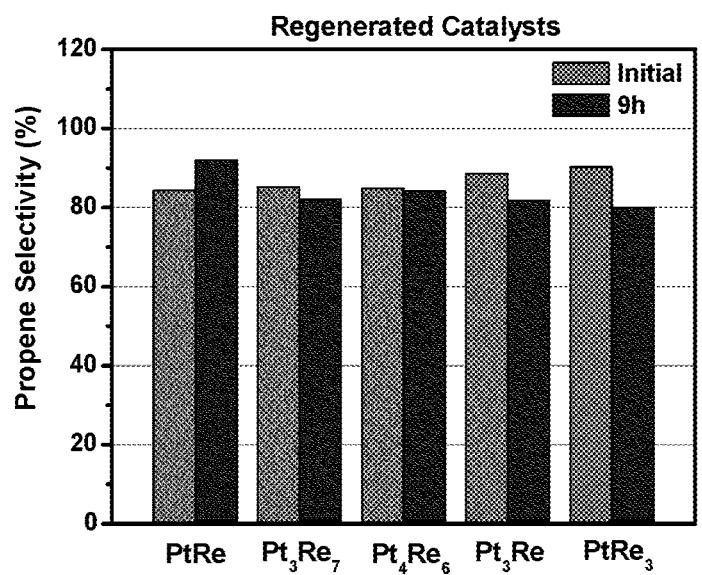

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to catalysts. Embodiments are related to alkane activation by single and bimetallic catalysts on amorphous and crystalline supports.

A first embodiment relates to alkane activation with single- or bi-metallic catalysts on crystalline mixed oxide supports, such as perovskites or fluorites. Certain embodiments $(La_xSr_{1-x})Cr_yFe_{1-y}O_{3-\delta}$ (LSCF) as a support for metal catalysts, where x is 0-1 (such as 0.3 to 0.7, further such as 0.75), y is 0-1 (such as 0.3 to 0.7, further such as 0.7, further such as 0.5) and $\delta$ less than 3 to 0. In one implementation LSCF-supported single-metal catalysts and in a second implementation, LSCF-supported bimetallic catalysts. Catalysts according to such embodiments are capable of converting a 100% methane feed the thermodynamic ratio of $C_2$ and $C_3$ products and hydrogen at 550-650° C. The thermal equilibrium is ca. 4% at 650° C. and this can be achieved at moderate space velocities. The catalyst operates for several hours (>4 h; unoptimized) and can be regenerated via calcination in air. Single center ions and bimetallic alloys on the surface of the crystalline perovskites (e.g., LSCF, $La_xSr_{1-x}Cr_yFe_{1-y}O_3$), such as $(La_xSr_{1-x})_{0.95}Cr_yFe_{1-y}O_3$.

They show high catalytic activity in propane dehydrogenation reaction, live longer than 10 hours, and could be simply regenerated by calcination in air. In these embodiments, the catalyst exhibit beneficial properties: supported, single atom catalysts are active for alkane dehydrogenation; the selectivity is far superior to thermal cracking; the lifetime of single-site catalysts is far superior to nanoparticle catalysts; the dehydrogenation rates of bi-metallic catalysts are superior to single-site catalysts; and the lifetime of bi-metallic alloy catalysts is far superior to single-metal nanoparticle catalysts.

A second embodiment relates to alkane activation with bi-metallic PtCo alloy catalysts on amorphous support. Supported PtCo alloy catalysts are active for alkane dehydrogenation. The selectivity is approaching 100%. The lifetime of PtCo alloy catalysts is far superior to Pt nanoparticle catalysts. The dehydrogenation rates of PtCo alloy catalysts are superior to Pt nanoparticle catalyst and single-site Co catalyst. In these embodiments, the catalyst exhibit beneficial properties: PtCo alloy catalysts are active for alkane dehydrogenation. For some embodiments, the selectivity approaches 100%. The lifetime of PtCo alloy catalysts is far superior to Pt nanoparticle catalysts; and the dehydrogenation rates of PtCo alloy catalysts are superior to Pt nanoparticle catalyst and single-site Co catalyst.

A third embodiment relates to production of $C_2$ and $C_2+$ alkanes on non-oxidative $CH_4$ coupling bimetallic catalysts. The catalytic materials use bifunctional bimetallic nanoparticles supported on the surface of amorphous support ($SiO_2$). They show high catalytic activity in NOCM reaction, live for several hours, and could be simply regenerated by calcination in air. In these embodiments, the catalyst exhibit beneficial properties: are active for NOCM; equilibrium conversion may be achieved at 650° C., as well as 550° C., with high $C_2H_4$ and $C_3H_6$ selectivity; the NOCM rates of bi-metallic catalysts are superior to known single-site catalysts (W/$SiO_2$, Ta/$SiO_2$). Further, the reaction pathway is $CH_4 \rightarrow C_2H_6$, $C_2H_4$, and $C_3H_6$. The lifetime of bi-metallic catalysts is about several hours, and the catalysts could be regenerated by calcination in air.

A fourth embodiment relates to barium For BZPY, the formula is $BaZr_{0.7}Pr_{0.1}Y_{0.2}O_x$ wherein x can also be 0 to 1.

a. Alkane Activation with Single- and Bi-metallic Catalysts on Crystalline Mixed Oxide Supports A third embodiment relates to production of $C_2$ and $C_2+$ alkanes on non-oxidative $CH_4$ coupling bimetallic catalysts. The catalytic materials use bifunctional bimetallic nanoparticles supported on the surface of amorphous support ($SiO_2$). They show high catalytic activity in NOCM reaction, live for several hours, and could be simply regenerated by calcination in air. Smaller particles are believed to be superior because they have more exposed reactive atoms. This material is an alloy in which the Pt atoms and ensemble are smaller than the number necessary to produce coke and/or cleave C—C bonds. Thus these catalysts are more selective to propylene/olefins than traditional catalyst. The precise ensemble number of Pt necessary to produce coke may be as small as single Pt atoms up to several; the exact number is still subject to more research. In the case of Ni, ensembles are broken up with (e.g.) S for steam reforming. The agent to break up ensemble size could be any element, but must be one that forms a material that is kinetically stable under the catalysis and regeneration conditions (if regeneration is needed). Note: kinetic vs thermodynamic stability is important since we may make alloys that are not directly on the phase diagram and the catalyst may evolve during reaction; the important thing is that we prepared it and used it.

In these embodiments, the catalyst exhibit beneficial properties: are active for NOCM; equilibrium conversion may be achieved at 650° C., as well as 550° C., with high $C_2H_4$ and $C_3H_6$ selectivity; the NOCM rates of bi-metallic catalysts are superior to known single-site catalysts (W/$SiO_2$, Ta/$SiO_2$). Further, the reaction pathway is $CH_4 \rightarrow C_2H_6$, $C_2H_4$, and $C_3H_6$. The lifetime of bi-metallic catalysts is about several hours, and the catalysts could be regenerated by calcination in air.

To test an embodiment of $(La_xSr_{1-x})_{0.95}Cr_yFe_{1-y}O_{3-\delta}$ (LSCF) based catalysts, $(La_{0.75}Sr_{0.25})_{0.95}Cr_{0.7}Fe_{0.3}O_{3-\delta}$ (LSCF) was synthesized using the Glycine-nitrate combustion method. The precursor was prepared by combining glycine with metal nitrates in their appropriate stoichiometric ratios in an aqueous solution. The precursor was heated to evaporate the excess water, yielding a viscous liquid. Further heating caused the precursor liquid to auto-ignite. Combustion was rapid and self-sustaining, with flame temperatures ranging from 1100 to 1450° C. After calcination in air at 650° C., the product was compositionally homogeneous with perovskite structure determined by XRD analysis and a specific surface area of ~20 m$^2$/g determined by BET analysis. Detailed synthetic procedure is described below.

Glycine (6.60 g, 88.14 mmol), $La(NO_3)_3$·$6H_2O$ (6.97 g, 16.10 mmol), $Sr(NO_3)_2$ (1.14 g, 5.37 mmol), $Cr(NO_3)_3$·$9H_2O$ (6.33 g, 15.82 mmol), and $Fe(NO_3)_3$·$9H_2O$ (2.74 g, 6.78 mmol) were dissolved in 44 mL deionized water. The solution was heated at 120° C. in a 4L stainless steel beaker to evaporate the excess water. After a viscous liquid is obtained, the temperature was increased to ~180° C. After ignition, brown powder was obtained (~80% yield). The powder was calcined at 650° C. in air for 6 hours, and then used as the support in the catalyst synthesis.

$Sm_{0.1}Ce_{0.9}O_2$ was also synthesized using the Glycine-nitrate combustion method using $Ce(NO_3)_3$·$6H_2O$ and $Sm(NO_3)_3$·$6H_2O$ as precursors combined with glycine in appropriate stoichiometric ratios in aqueous solution. Glycine(26.04 g, 340 mmol), $Ce(NO_3)_3$·$6H_2O$ (67.78 g, 153 mmol), $Sm(NO_3)_3$·$6H_2O$ (7.71 g, 17 mmol) were dissolved in 400 mL water to make the total volume 500 mL. The solution was heated at 120° C. in a stainless steel beaker to evaporate the excess water. After a viscous liquid is obtained, the temperature was increased to 140° C. After ignition, yellow-white powder was obtained (~60% yield). The powder was calcined at 650° C. in air for 6 hours, and then used as the support in the catalyst synthesis.

i. LSCF-supported Single-metal Catalysts

LSCF-supported Mo catalyst, Mo/LSCF, was synthesized using the incipient wetness impregnation (IWI) method by impregnating $(NH_4)_6Mo_7O_{24}$·$4H_2O$ aqueous solution onto LSCF powder based on the specified Mo weight loading (0.1 wt % in this case), followed by dryness in air at 120° C. and calcination in air at 650° C. Other LSCF-supported single-metal catalysts were synthesized using a similar procedure. The detailed synthetic procedure of the Mo/LSCF is shown below as an example.

0.1 g of $(NH_4)_6Mo_7O_{24}$·$4H_2O$ was dissolved in 10 mL of DI $H_2O$, and 0.9 mL (equal to the pore volume of 2.0 g of LSCF) of the aqueous solution was impregnated onto 2.0 g LSCF powder and then dried at 120° C. in air. The catalyst was then calcined in air at 650° C. for 6 hours before the dehydrogenation test. LSCF-supported Ru catalyst, Ru/LSCF, was synthesized using a similar recipe with Ru(NO$_3$)$_2$ precursor.

LSCF-supported Co catalyst, Co/LSCF, was synthesized using strong electrostatic adsorption (SEA) method under basic condition (pH=10). The detailed synthetic procedure of the Co/LSCF is shown below. 0.8 g of Co(NH$_3$)$_6$Cl$_3$ was dissolved in 100 mL of DI H$_2$O and adjusted pH value to 10. In a separate beaker, 5 g of LSCF dispersed with 350 mL DI water, and the pH was adjusted to 10 by adding NH$_4$OH aqueous solution. The Co solution and LSCF slurry was mixed together, and stirred for 1 hour. Then the solution was removed by filtration, and the catalyst was rinsed several time with DI water and dried at 150° C. The catalyst was then calcined in air at 650° C. for 6 hours before the dehydrogenation test.

Catalyst testing was performed in a vertical, ⅜" quartz tube reactor equipped with gas flow meters and gas chromatography (GC) for product analysis. For each experiment, 0.1 of catalyst was supported on quartz wool within the quartz tube. Initially, the catalyst was flushed with Ar at 30 mL/min at room temperature, and then, the temperature of the reactor was raised to the reaction temperature (i.e., 500° C. or 550° C.) and given ample time to stabilize. Some of the catalysts were reduced with 3% H$_2$/Ar before the propane dehydrogenation test. The propane is 2.3% balanced with Ar (Airgas USA, LLC). Product concentrations were analyzed by a flame ionization detector (FID) using H$_2$ (99.999%, Airgas USA, LLC) and air (<2 ppm H$_2$O, Airgas USA, LLC).

The catalytic results of selected catalysts are presented in Table 1.

TABLE 1

Rates and selectivities for propane dehydrogenation of LSCF supported catalysts

| Catalyst | Dehydrogenation Rate (mmolC$_3$ · h$^{-1}$ · g$^{-1}$cat) | Dehydrogenation Selectivity (%) | Temperature (° C.) |
|---|---|---|---|
| LSCF | 0.090 | 23.0 | 550 |
|  | 0.031 | 88.5 | 500 |
| Co/LSCF | 0.060 | 60.0 | 550 |
| Mo/LSCF | 0.043 | 96.3 | 500 |
| Ru/LSCF | 0.092 | 95.8 | 500 |

Both Mo/LSCF and Ru/LSCF exhibited higher dehydrogenation rate compared with the bare LSCF under the same reaction conditions with Ru-LSCF showing the highest dehydrogenation rate (0.092 mmol·h$^{-1}$·g$^{-1}$ cat), and they also show very high propylene selectivity (above 95%). Without being treated in hydrogen, Ru-LSCF exhibited dehydrogenation activity essentially equal to the unmodified LSCF. After pretreatment in H$_2$ at 650° C. for 30 mins, Ru-LSCF catalyst gave an initial propane dehydrogenation rate of 0.092 mmol·h$^{-1}$·g$^{-1}$ cat with propene >95% selectivity. Co/LSCF does not show high dehydrogenation reactivity, and EDX analysis shows that Cr and Sr were partially removed during the SEA synthesis under basic conditions, which changed the surface structure of the LSCF support.

(1) Ce-doped LSCF Catalysts

The Ru/LSCF, Co/LSCF and Mo/LSCF catalysts were synthesized using a surface modification of LSCF. An alternative approach is to integrate the catalytically active metals during the Glycine nitrate combustion synthesis of LSCF. We proposed doping a small amount of Ce into LSCF should keep the perovskite structure and high conductivity of LSCF. It has also been shown that a similar LSCF with 5% Ce dopant gave the highest performance in syn gas fuel cell. So a 5% Ce-doped LSCF (Ce-LSCF) was synthesized using Glycine nitrate combustion method. XRD pattern confirmed that the perovskite structure remained in Ce-LSCF.

The synthesis of the 5% Ce-LSCF was detailed below. Glycine (15.02 g, 200 mmol), La(NO$_3$)$_3$.6H$_2$O (7.71 g, 17.8 mmol), Ce(NO$_3$)$_3$.6H$_2$O (0.54 g, 1.25 mmol), Sr(NO$_3$)$_2$ (1.26 g, 5.9 mmol), Cr(NO$_3$)$_3$.9H$_2$O (7.00 g, 17.5 mmol), and Fe(NO$_3$)$_3$.9H$_2$O (3.03 g, 7.5 mmol) were dissolved in 100 mL deionized water. The solution was heated at 120° C. in a stainless steel beaker to evaporate the excess water. After a viscous liquid is obtained, the temperature was increased to ~180° C. After ignition, brown powder was obtained. The powder was calcined at 650° C. in air for 6 hours, and then used in the catalyst test.

Ce-LSCF showed very high dehydrogenation rate. After reduction at 650° C. with H$_2$, Ce-LSCF gave a reaction rate of 0.651 mmol·h$^{-1}$·g$^{-1}$ cat, with above 90% propene selectivity. Reduction with H$_2$ at 500° C. led to a higher rate of 3.111 mmol·h$^{-1}$·g$^{-1}$ cat. It is the highest reaction rate among all the LSCF catalysts at 500° C. The propene also went up to ~98%. It should be noted that the rate was calculated at equilibrium conversion, so the real dehydrogenation rate should be higher than 3.111 mmol·h$^{-1}$·g$^{-1}$ cat.

The dehydrogenation was also tested at 450° C. Equilibrium conversion was also obtained, and the rate was calculated as 1.416 mmol·h$^{-1}$·g$^{-1}$ cat. with about 90% propene selectivity. Ce-LSCF showed very high dehydrogenation activity, but the stability still needs to be improved. Ce-LSCF deactivates in about 1 hour on stream. Spent Ce-LSCF could be simply regenerated by treatment with air at 500° C. Most of the dehydrogenation rate could be resumed with high propene selectivity (98%). After treatment with NH$_4$OH (pH=10) aqueous solution, Ce-LSCF lost most of the activity. The dehydrogenation rate dropped to 0.384 mmol·h$^{-1}$·g$^{-1}$ cat. EDX analysis showed that the NH$_4$OH treatment removed most of the surface Cr species, which suggests that the surface Cr species in Ce-LSCF are responsible for the high dehydrogenation activity.

TABLE 2

Propane dehydrogenation results of Ce-LSCF catalysts

| Catalyst | Dehydrogenation Rate (mmol · h$^{-1}$ · g$^{-1}$cat) | C$_3$H$_6$ selectivity (%) | Reaction Temperature (° C.) | Treatment |
|---|---|---|---|---|
| Ce-LSCF | 0.651 | 92.5 | 500 | Reduced at 650° C. |
|  | 3.111 | 98.2 | 500 | Reduced at 500° C. |
|  | 1.416 | 89.9 | 450 | Reduced at 500° C. |
| Ce-LSCF Regen. | 1.830 | 98.0 | 500 | Regenerated in air at 500° C. |
| NH$_4$OH treated Ce-LSCF | 0.384 | 90.9 | 500 | Reduced at 500° C. |
| 0.1% Ce@LSCF | 1.830 | 95.9 | 500 | Reduced at 500° C. |

0.1 g of catalyst was used for the dehydrogenation using 2.28% C$_3$H$_8$ in Ar with a flow rate of 30 mL/min.

A control experiment was carried out by impregnating 0.1% $Ce(NO_3)_3$ onto the surface of LSCF yielding 0.1% Ce@LSCF catalyst. Interestingly, 0.1% Ce@LSCF showed a dehydrogenation rate of 1.83 mmol·h$^{-1}$·g$^{-1}$ cat suggesting that the presence of Ce plays a crucial role in activating the surface Cr species in LSCF.

(2) LSCF-supported Bimetallic Catalysts

All the bimetallic catalysts were synthesized using the incipient wetness co-impregnation method by mixing the two metal salts with specified ratio in aqueous solution and co-impregnated onto the LSCF support. The synthesis of PtGa/LSCF is shown below as an example.

1.0 mL of 0.01 M $Pt(NH_3)_4(NO_3)_2$ was mixed with 1.0 mL of 0.01 M $Ga(NO_3)_3$, and then the mixed solution was impregnated onto 1.0 g of LSCF using an impregnation-dry-impregnation procedure, i.e., ~0.5 mL of the mixed solution is impregnated onto 1.0 g of LSCF, and then the sample is dried in air at 120° C. for ~30 minutes. After cooling to room temperature, another 0.5 mL of the mixed PtGa solution was impregnated. The impregnation-dry-impregnation procedure is repeated until the PtGa mixed solution was all impregnated. The catalyst was then calcined at 650° C. in air for 6 hours before the dehydrogenation test. The dehydrogenation results of selected bimetallic catalysts are summarized below.

$Pt_xRe_y$/LSCF catalysts generally show high dehydrogenation rates. All the catalysts deactivate; however, the catalysts with the Pt/Re ratio <1 show TOF >0.01 s$^{-1}$ after about 9 hours on stream. Regenerated PtRe/LSCF and PtRe$_3$ retained TOF close to 0.01 s$^{-1}$ after about 10 hours on stream. It should be noted that the regenerated PtRe$_3$ catalyst did not show the original high dehydrogenation rate, but the stability was found to be very good at a TOF of ca. 0.01 s$^{-1}$. The propene selectivities are around 70%-90% for the fresh catalysts at high conversions; while the propene selectivities of the regenerated catalysts are about 80%-90% (see FIG. 2).

Figure 3A:
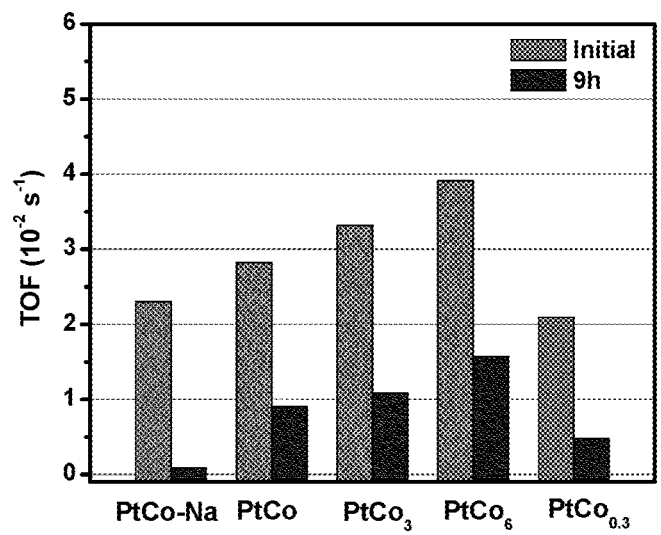
FIGS. 3A-3B show propane dehydrogenation of $Pt_xCo_y$/LSCF catalysts with various metal ratios (Pt 0.1 wt %).
Figure 3B:
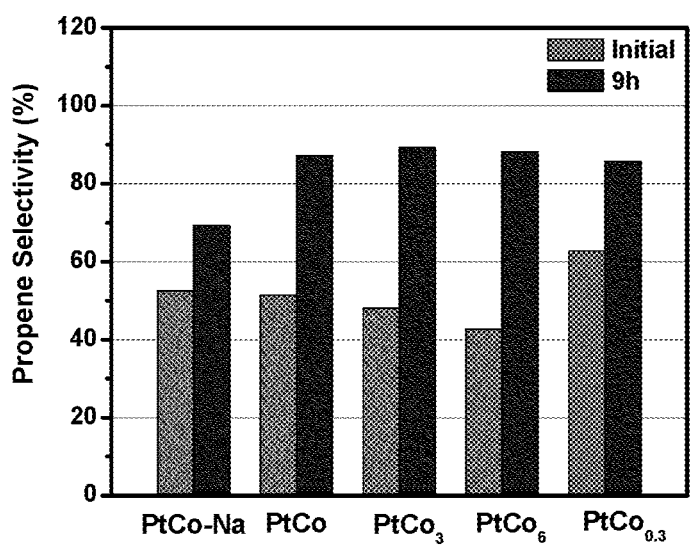

High dehydrogenation rates and good stability were observed for $Pt_xCo_y$/LSCF catalysts. As shown in FIG. 3, increasing the Co/Pt ratio led to high dehydrogenation rate and high propene selectivity. At high conversion, the propene selectivities were around 60%, but at lower conversions, the propene selectivities went up to about 90%.

Figure 4:
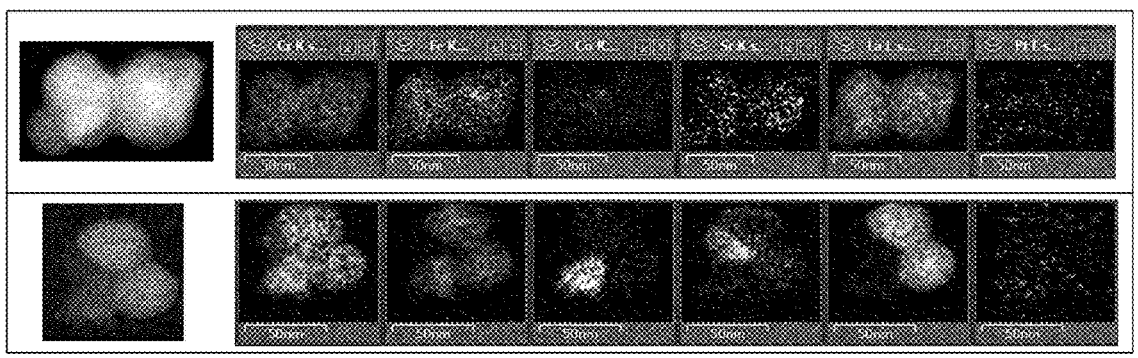
FIG. 4 shows STEM images of two particles of Pt/Co on LSCF. The top shows a well-dispersed particle, the bottom shows significant Co localization. Note about homogeneity: more particles were well-dispersed than not (ca. 5:1 or more).

The PtCo on LSCF were also examined by scanning transmission electron microscopy (STEM). Most particles were found to be quite homogeneous in metal dispersion by element mapping (FIG. 4, top). However, some were found to have significant localization of phases (e.g. Co, Sr, FIG. 4, bottom). Both of these particles are from the same synthesis. A rough analysis shows that most of the material is well-dispersed (ca. 5:1).

Figure 5A:
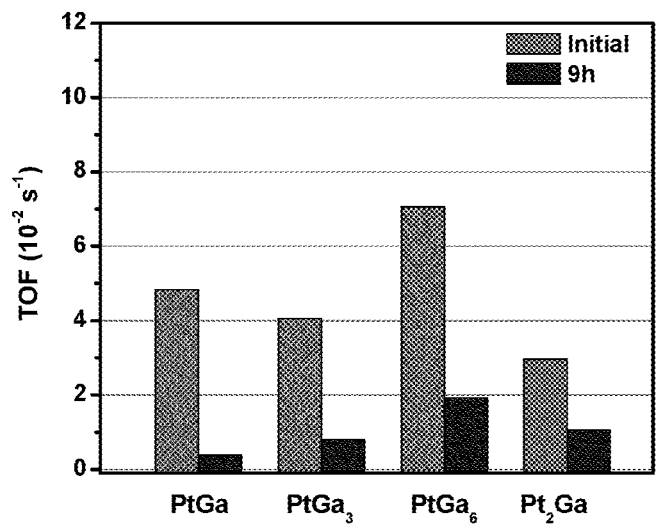
FIGS. 5A-5B show propane dehydrogenation of $Pt_xGa_y$/LSCF catalysts with various metal ratios (Pt 0.1 wt %).
Figure 5B:
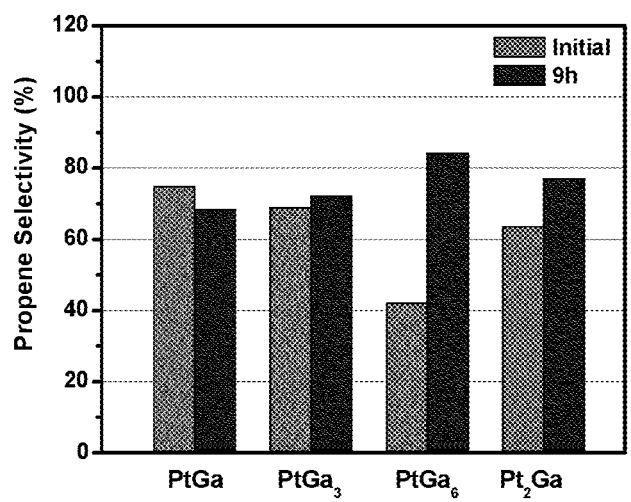

$Pt_xGa_y$/LSCF catalysts with various Pt/Ga ratios were also synthesized and evaluated for propane dehydrogenation. As shown in FIG. 5, all the $Pt_xGa_y$/LSCF catalysts showed an initial rate above TOF of 0.01 s$^{-1}$. For most catalysts, the propene selectivity was about 70%, and no significant change of the selectivity was observed after 9 hours on stream.

Further decreasing the metal loadings and increasing the Ga/Pt ratio to 37 led to a significant increase of the dehydrogenation TOF, as shown in FIG. 6. It should be noted that the dehydrogenation rate (per gram catalyst) are very similar for those catalysts, which suggests that the low catalyst loading gave higher Pt dispersion and higher ratio of active sites.

Figure 6A:
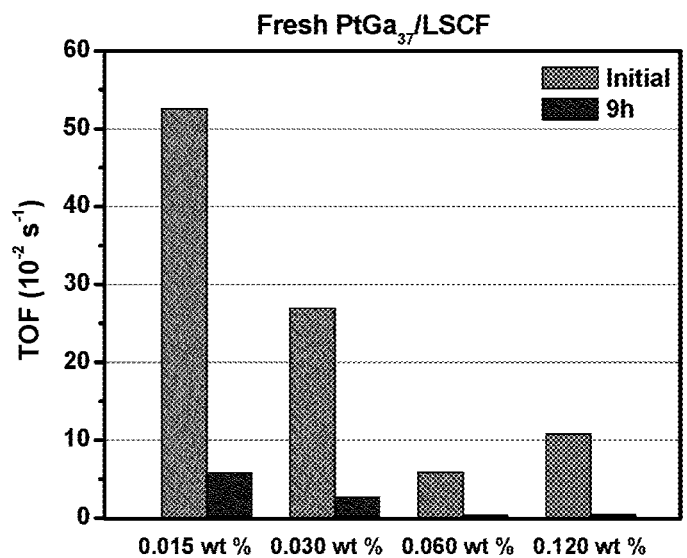
FIGS. 6A-6F show propane dehydrogenation of $Pt_xGa_y$/LSCF catalysts with various metal loadings.
Figure 6B:
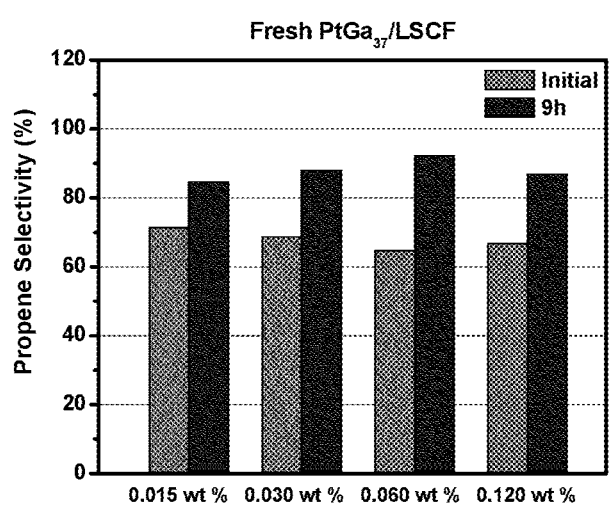
Figure 6C:
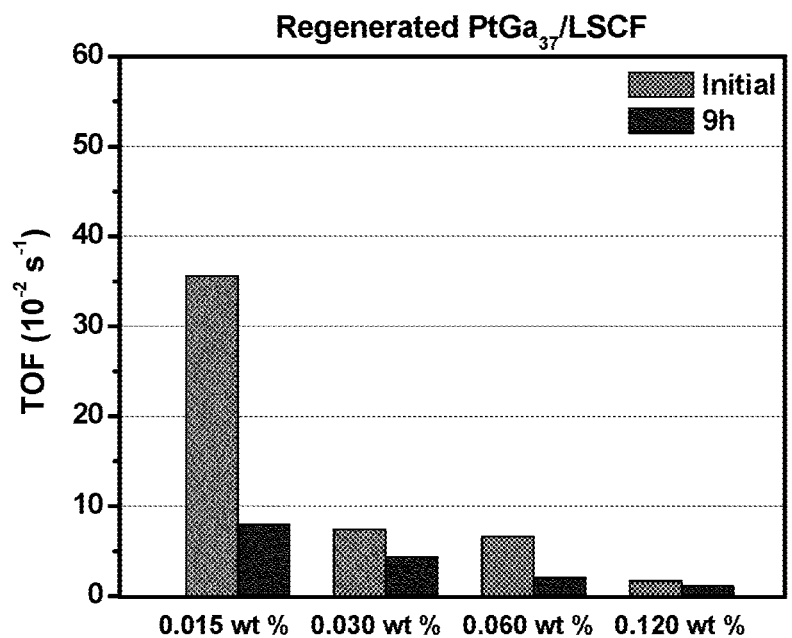
Figure 6D:
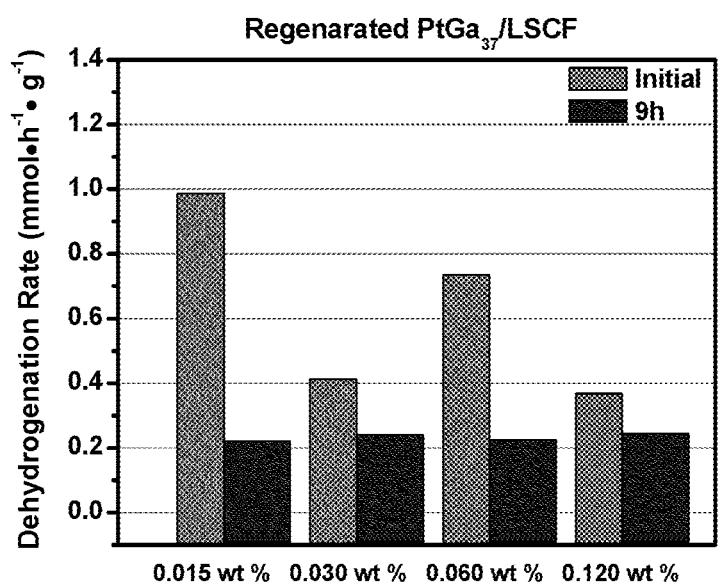
Figure 6E:
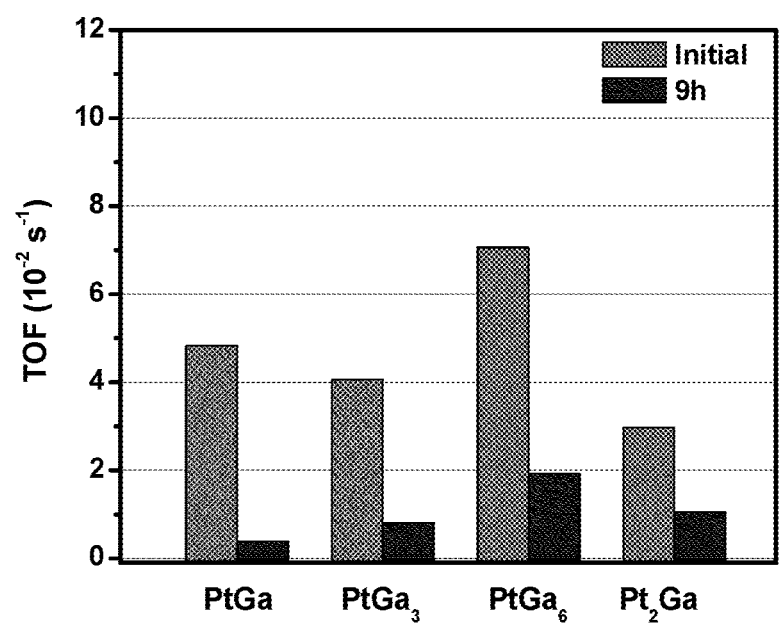

The ratio of Cr to Fe would affect whole material electron resistance, and the ratio is also importance to whole structure stability. The higher of ratio of Cr to Fe can decrease resistance of material, but also increase impurity phase of perovskite. From XRD pattern, it has been observed that higher ratio of Cr to Fe would affect separating out of Cr oxide and Sr oxide, however, if it decreased of ratio of Cr to Fe, it also highly decreased conductivity of material. Thus, it's importance to balance the ratio of Cr and Fe. For one embodiment, the maximum ratio of Cr to Fe with a structure stable is 3. Further decreasing the metal loadings and increasing the Ga/Pt ratio to 37 led to a significant increase of the dehydrogenation TOF, as shown in FIG. 6E. Even after regeneration, the TOF of some of the catalysts at 9 hours on stream were still much higher than the milestone requirement. It should be noted that the dehydrogenation rate (per gram catalyst) are very similar for those catalysts, which suggests that the low catalyst loading gave higher Pt dispersion and higher ratio of active sites.

Figure 6F:
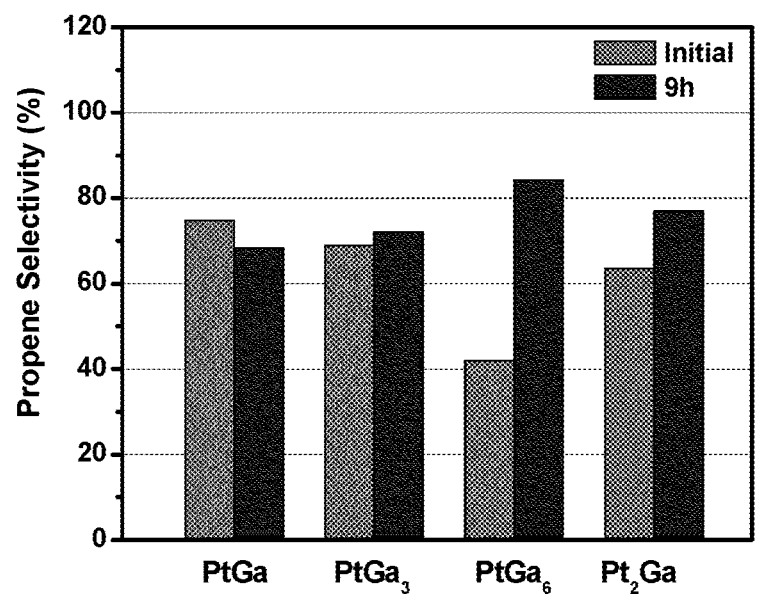

$Pt_xGa_y$/LSCF catalysts with various Pt/Ga ratios were also synthesized and evaluated for propane dehydrogenation. As shown in FIG. 6F, all the $Pt_xGa_y$/LSCF catalysts showed an initial rate above TOF of 0.01 s$^{-1}$. After 9 hours on stream, the PtGa$_6$ and Pt$_2$Ga/LSCF catalysts remained a higher TOF than the milestone. For most catalysts, the propene selectivity was above 70%, and it has no significant change of the selectivity was observed after 9 hours on stream.

Figure 10:
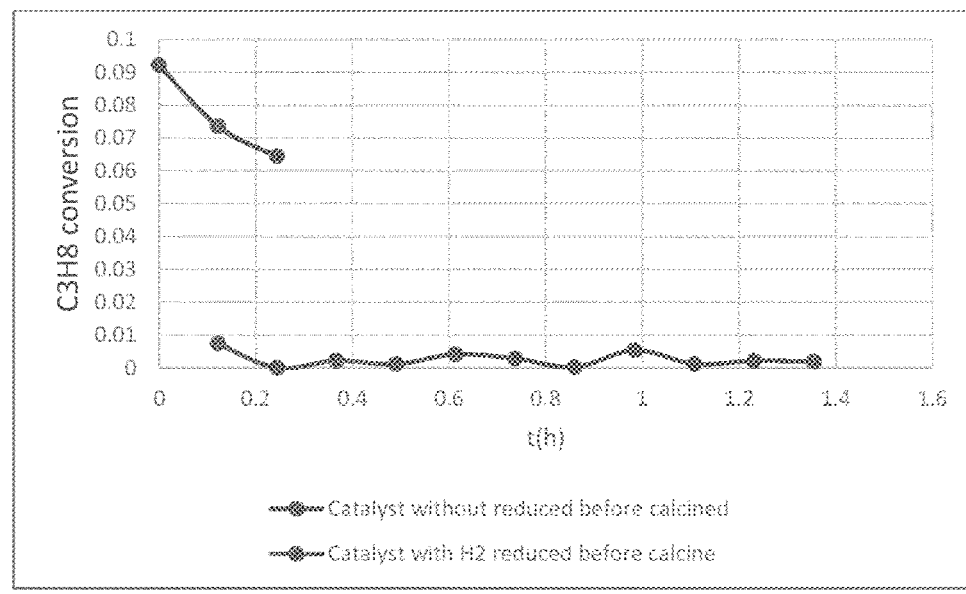
FIG. 10 shows a $C_3H_8$ conversion with and without $H_2$ reduced.
Figure 11A:
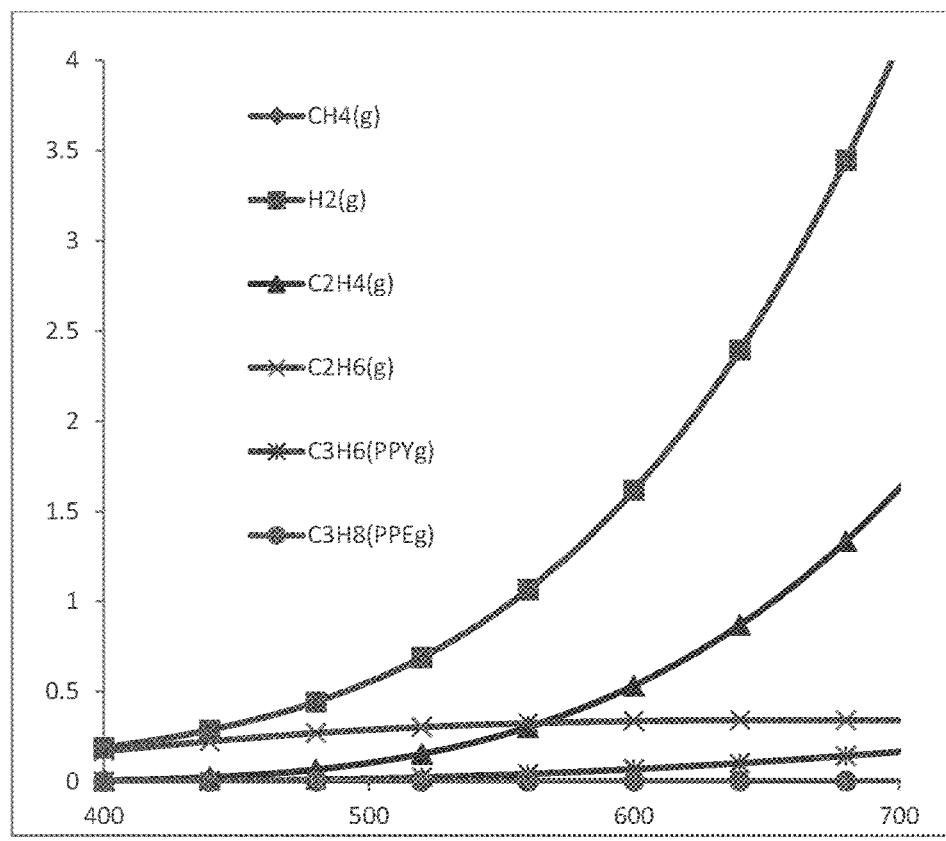
FIGS. 11A-11B are plots of the thermodynamics (calculated using HSC) and a kinetic trace for one of the catalysts.
Figure 11B:
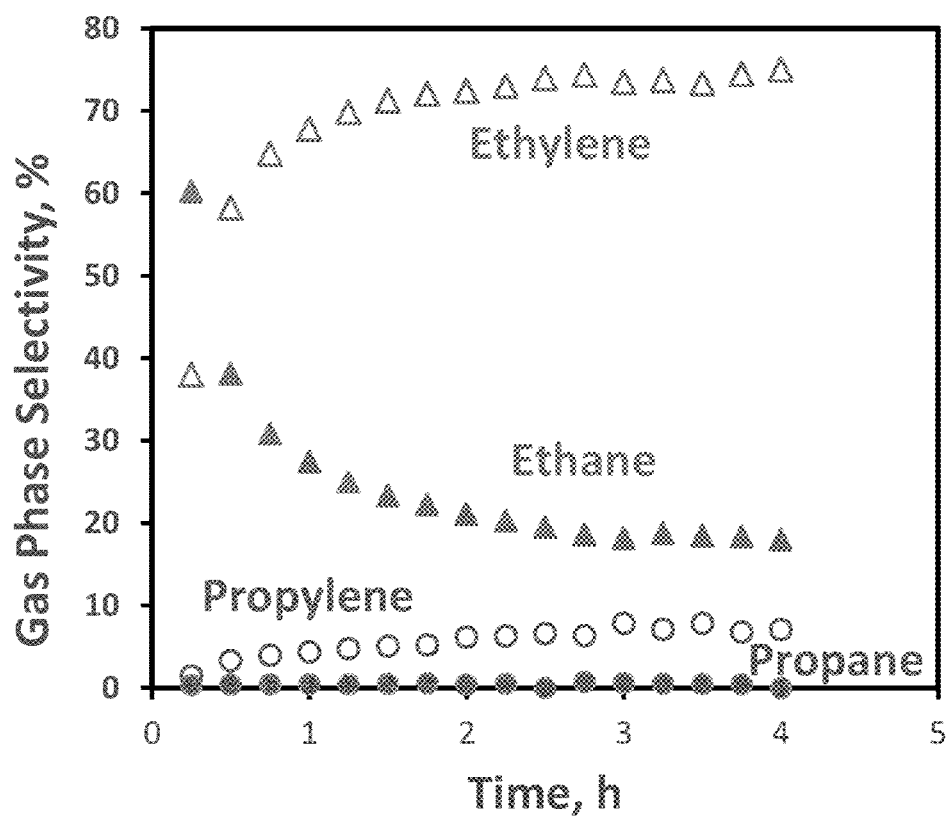

Compared to catalyst without pretreatment of H$_2$, the catalyst with pretreated in H$_2$ keeps propane dehydrogenation catalytic after calcined in very high temperature. It means that material for fuel cell still keeps catalytic activity in very high temperature. It's both benefit for fabricating fuel cell and making fuel cell work in very high temperature. FIG. 10 illustrates $C_3H_8$ conversion.

Figure 7A:
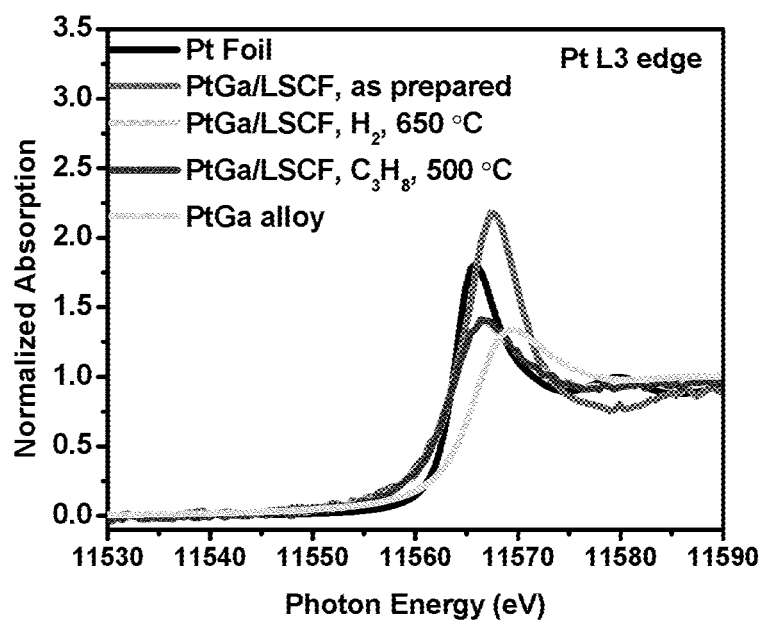
FIG. 7A shows Pt edge XANES.
Figure 7B:
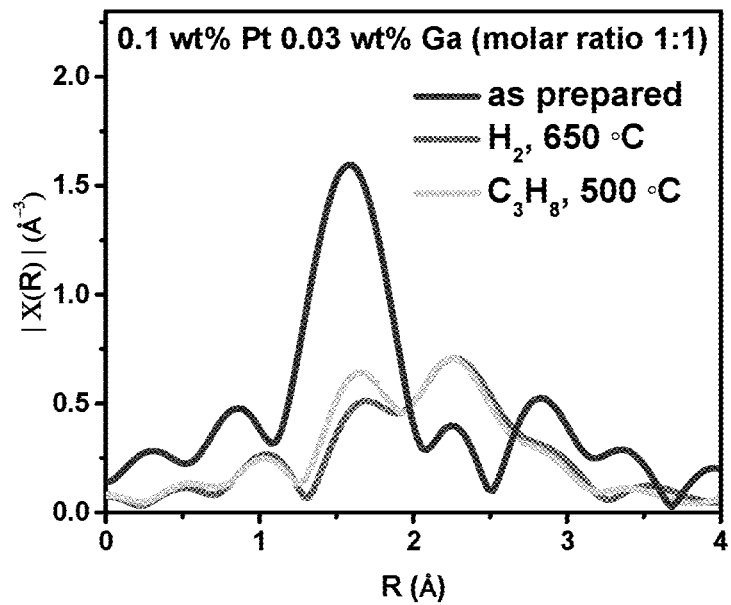
FIG. 7B shows EXAFS spectra for select PtGa alloys.
Figure 7C:
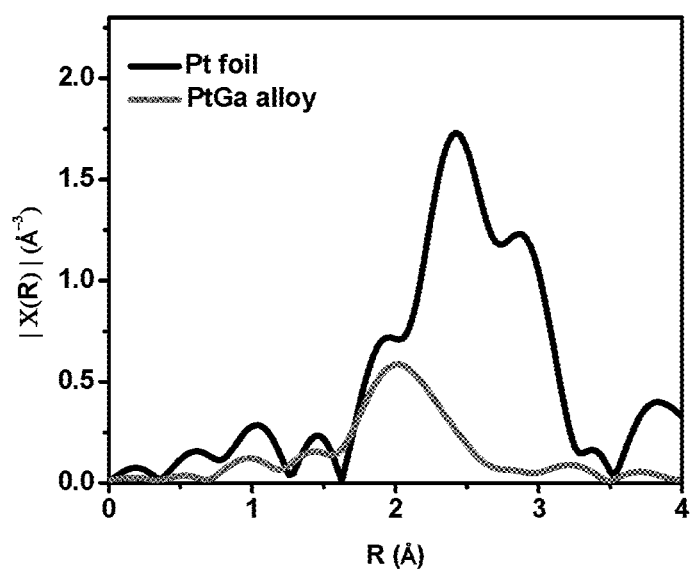
FIG. 7C shows EXAFS spectra for Pt foil compared to PtG alloy.
Figure 8:
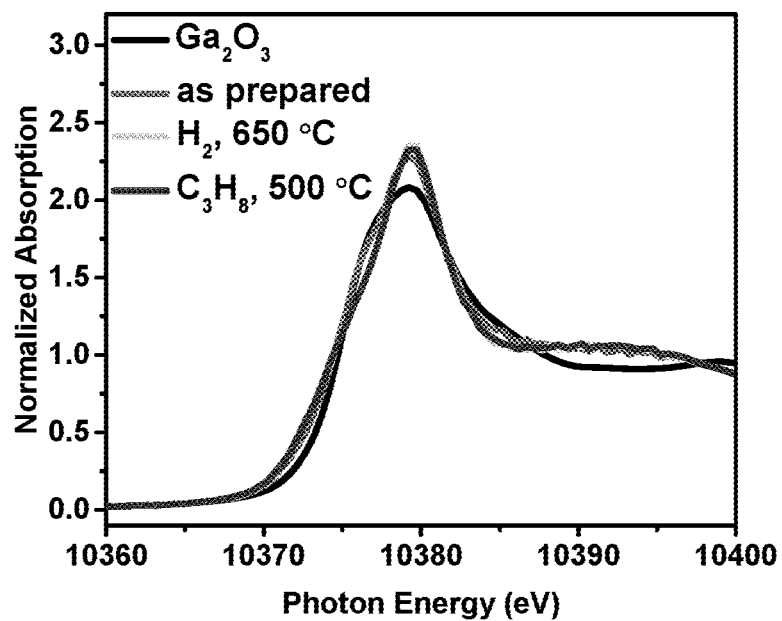
FIG. 8 shows Ga edge XANES.
Figure 9:
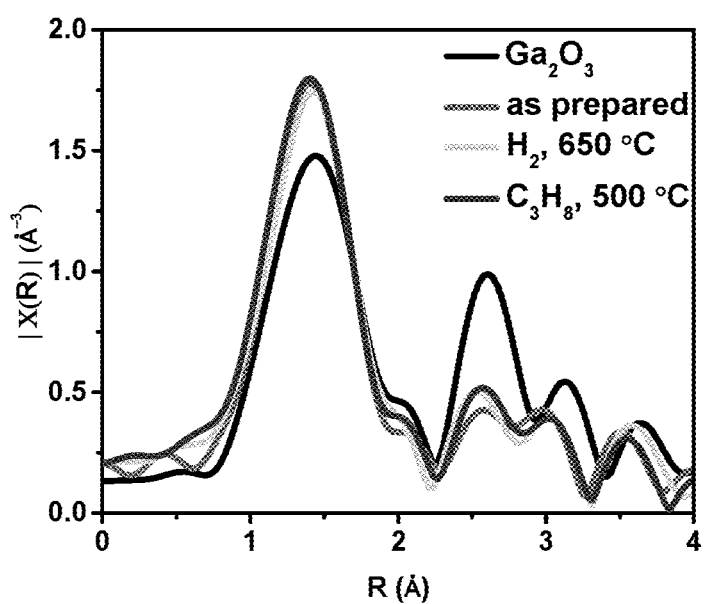
FIG. 9 shows EXAFS spectra.

As shown in FIG. 7, the Pt in PtGa/LSCF catalyst is only partially reduced under either H$_2$ or $C_3H_8$ treatment. PtGa alloy was not observed under reaction conditions or after H$_2$ treatment at 650° C. Both Pt—O and Pt—Pt scatterings were observed in the EXAFS spectra, but no Pt—Ga scattering was observed, which is consistent with the XANES data. Lack of big second shells in the EXAFS spectra suggests that the catalyst contains very small Pt particles in both as-prepared and working catalysts.

The Ga K-edge XAFS data suggest that the Ga species under reaction conditions and after H$_2$ treatment remained as Ga(III), and no Ga(I) or Ga(0) was identified. The Ga species were mainly 6-coordinated with oxygen atoms only and remained the same under dehydrogenation conditions.

b. Alkane Activation with Bi-metallic PtCo Alloy Catalysts on Amorphous Support $SiO_2$-supported PtCo alloy catalysts were synthesized using a sequential grafting method. Co was grafted onto the $SiO_2$ surface using the strong electrostatic adsorption (SEA) method. Alternatively, other deposition techniques such as, but not limited to CVD and ALD, may be used. The selected deposition technique should minimize the unalloyed/large ensembles of the catalytic metal. After the $SiO_2$-supported Co was calcined, Pt precursor was impregnated onto the $SiO_2$ surface. Reduction with H$_2$ leads to the formation of the alloy catalyst. Detailed synthesis of the catalyst is shown below using the 0.1 wt % Pt 2 wt % Co/$SiO_2$ as an example. 20 g of silica (Davisil 646, 35-60 mesh, 300 m$^2$/g and 1.1 cm$^3$/g, Aldrich) were suspended in approximately 200 mL of deionized water. The pH of the solution was adjusted to about 11 using concentrated ammonium hydroxide (NH$_4$OH, Aldrich). In a separate flask, 5.00 g of Co(NH$_3$)$_6$Cl$_3$ (Aldrich) was dissolved in 50 mL of deionized water, and the pH adjusted to 11 with NH$_4$OH. The basic Co(III) solution was rapidly added to the silica and stirred for 10 min at room temperature. The solid was allowed to settle for 5 min and the solution decanted. The resulting wet powder was vacuum filtered, rinsed several times with deionized water, and dried at room temperature followed by drying overnight in air at 125° C. Subsequently, the catalyst was calcined by ramping over 1 h to 300° C. and holding for 3 h. Total cobalt loading by elemental analysis is 2.1 wt %. PtCo alloy catalysts with various Pt loadings were synthesized by impregnating Pt(NH$_3$)$_4$(NO$_3$)$_2$ aqueous solution onto the Co/SiO$_2$. Pt(NH$_3$)$_4$(NO$_3$)$_2$ solution (0.01 M, 0.50 mL) was firstly diluted with 1.5 mL DI H$_2$O, and then impregnated onto the 2% Co/SiO$_2$ using the incipient wetness impregnation technique. After drying in air at 120° C., the catalyst was calcined in air at 650° C. for 6 hours before the dehydrogenation test.

Catalyst testing was performed in a vertical, ⅜" quartz tube reactor equipped with gas flow meters and gas chromatography (GC) for product analysis. For each experiment, a specified amount of catalyst was supported on quartz wool within the quartz tube. Initially, the catalyst was flushed with Ar at 30 mL/min at room temperature, and then, the temperature of the reactor was raised to the reaction temperature (i.e., 500° C. or 450° C.) and given ample time to stabilize. The catalysts were reduced with 3% H$_2$/Ar before the propane dehydrogenation test. The propane is 2.3% balanced with Ar (Airgas USA, LLC). Product concentrations were analyzed by a flame ionization detector (FID) using H$_2$ (99.999%, Airgas USA, LLC) and air (<2 ppm H$_2$O, Airgas USA, LLC).

Figure 12A:
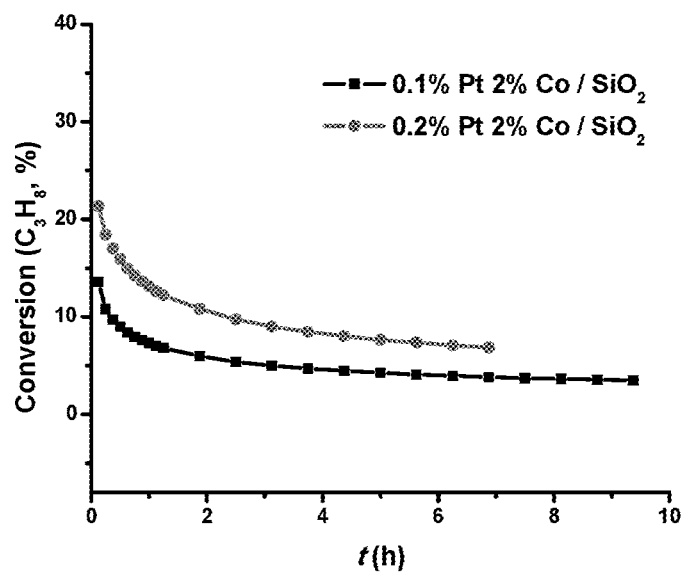
FIG. 12A is a plot of $C_3H_8$ conversion by PtCo/SiO$_2$ at 500° C.
Figure 12B:
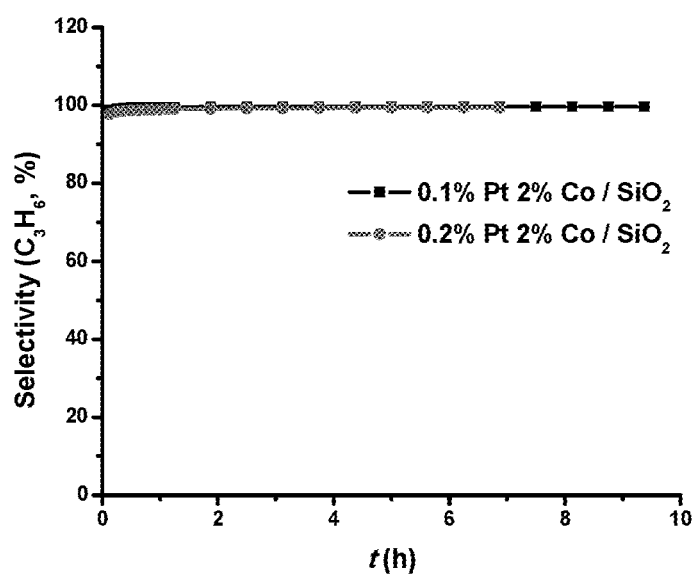
FIG. 12B is a plot of selectivity (20 mg of the PtCo/SiO$_2$ catalyst was diluted with SiO$_2$ to 200 mg, 2.30% $C_3H_8$/Ar with a flow rate of 55 mL/min).
Figure 13A:
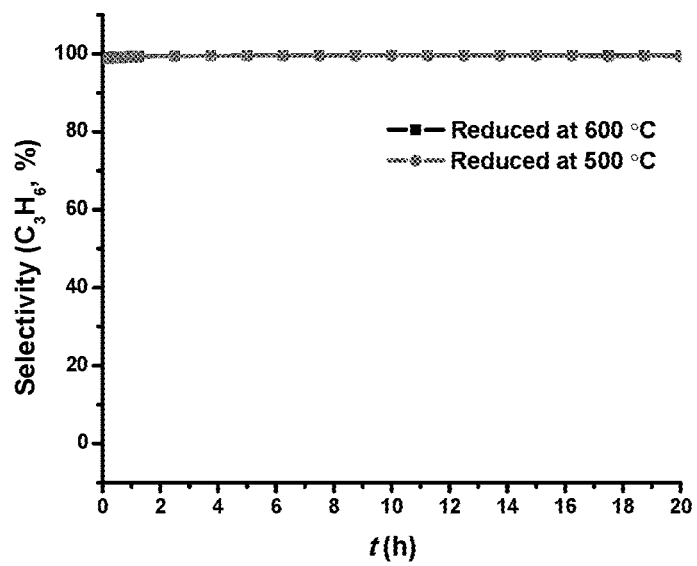
FIG. 13A is a plot of $C_3H_8$ selectivity for $Pt_xCo_y$/SiO$_2$ at 450° C.
Figure 13B:
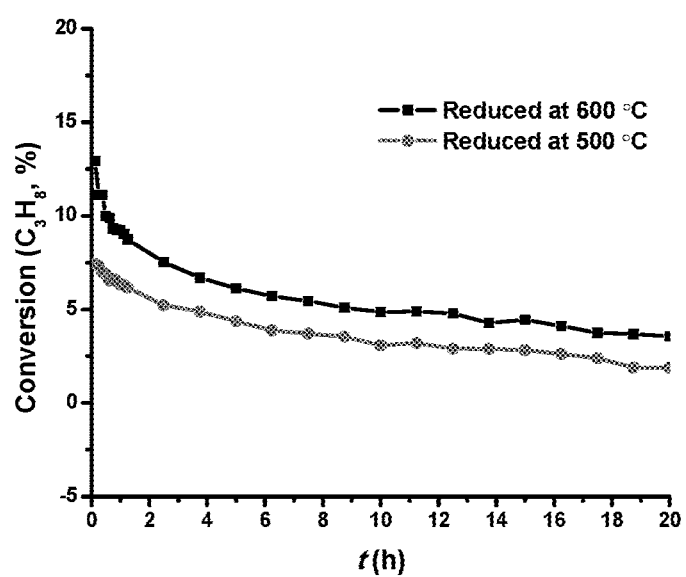
FIG. 13B is a plot of selectivity.
Figure 13C:
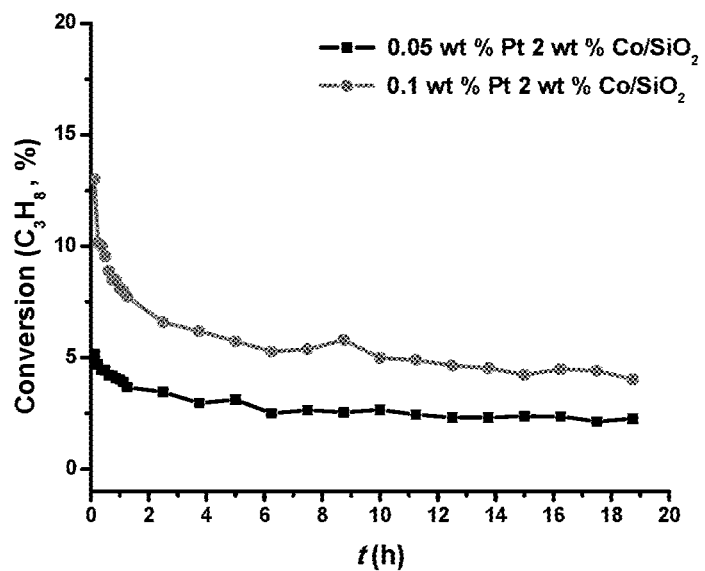
FIG. 13C is a plot of conversion based on loading.
Figure 13D:
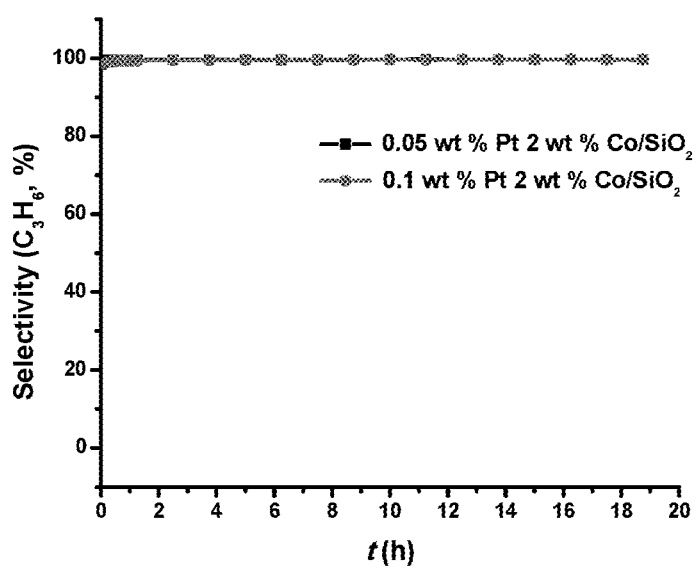
FIG. 13D is a plot of selectivity based on loading (30 mg of the PtCo/SiO$_2$ catalyst was diluted with SiO$_2$ to 200 mg, 2.30% $C_3H_8$/Ar with a flow rate of 85 mL/min).

The propane dehydrogenation results on 0.1% Pt2% Co/SiO$_2$ at 500° C. are shown in FIG. 12. At differential conversion (~10%), the catalyst 0.1 wt % Pt 2 wt % Co/SiO$_2$ gave an initial TOF of 0.90 s$^{-1}$, and the TOF levels off after three hours on stream at 0.46 s$^{-1}$. The propene selectivity approaches 100%, and no further deactivation was observed in the 10-hour test. Increasing the Pt loading to 0.2 wt % led to an increase of the propane conversion while maintaining the propene selectivity.

Further tests on Pt$_x$Co$_y$/SiO$_2$ were done at 450° C. to maintain differential (lower) conversion (~5%). As shown in FIG. 13, the dehydrogenation results of Pt$_x$Co$_y$/SiO$_2$ under various reduction temperatures showed that higher reduction temperature (600° C.) gave high dehydrogenation rates than lower temperature (500° C.). Reducing the Pt loading from 0.1 wt % to 0.05 wt % (keeping the Co loading the same) led to half of the propane conversion which gives the same TOF per Pt, which is suggesting that either Pt or PtCo alloy is the active catalyst.

The PtCo on SiO2 were examined by transmission electron microscopy (TEM). PtCo particle size is around 1-2 nm, and have very well dispersion on SiO$_2$ support by element mapping (FIG. 10).

Temperature vary from 723K to 743K. According to first order surface reaction, activation energy was calculated by rate constants. And high flow rate, low temperature and low loading of catalyst are ways to control low propane dehydrogenation conversion. At low conversion level, the concentration of C3H8 keeps almost same, the rate constant is proportional to TOF of reaction. The activation energy calculated by slope was 9.63 kcal/mol.

Figure 14:
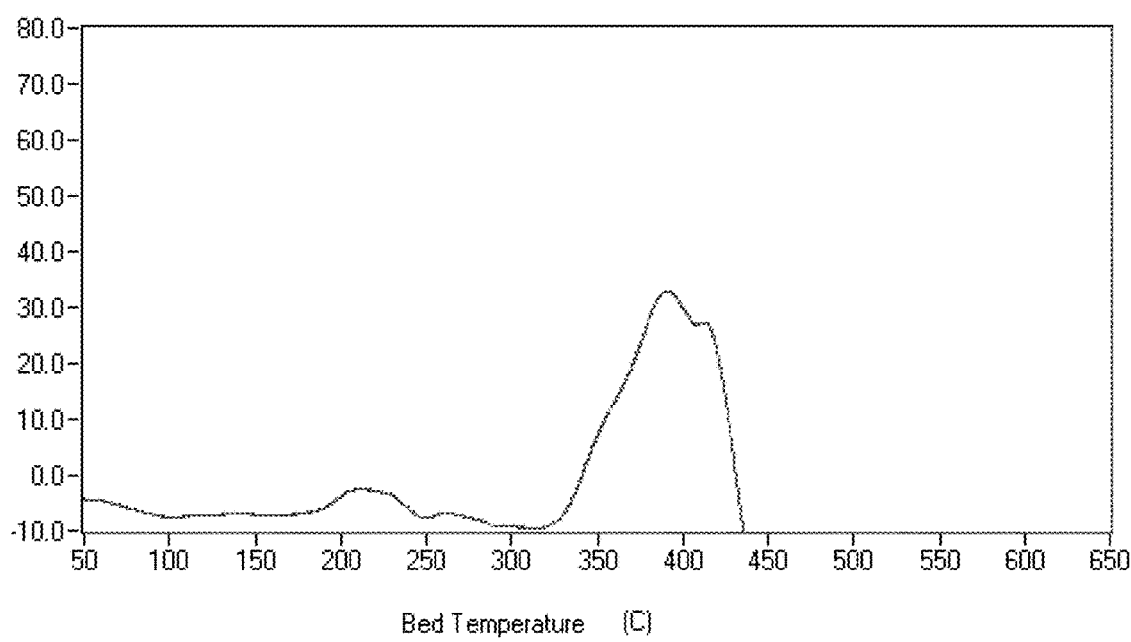
FIG. 14 shows TPR plots of 0.2 wt % Pt 2 wt % Co/SiO$_2$ on a LSCF support.
Figure 15:
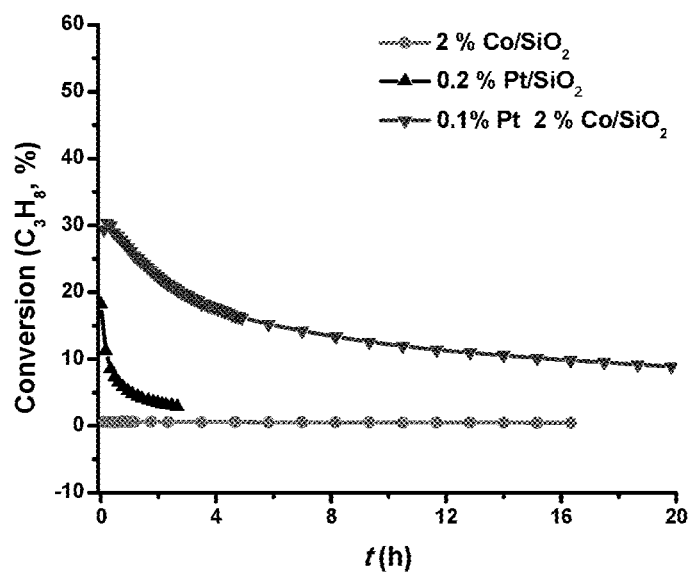
FIG. 15 is a plot of $C_3H_8$ dehydrogenation of $Pt_xCo_y$/SiO$_2$ at 500° C. (200 mg of the PtCo/SiO$_2$ catalyst, 2.30% $C_3H_8$/Ar with a flow rate of 20 mL/min).

A TPR (temperature programmed reduction) experiment was carried out to understand the reduction in the catalysts activation process of 0.2 wt % Pt 2 wt % Co/SiO$_2$. As shown in FIG. 14, a small peak at about 220° C. was observed, which could be assigned to the Pt reduction, as well as a broad peak at about 400° C. which corresponds to the reduction of Co. 2 wt % Co/SiO$_2$ does not show dehydrogenation activity under the same reaction conditions, while the 0.2 wt % Pt/SiO$_2$ shows much lower dehydrogenation rate and stability under the same reaction conditions, Pt$_x$Co$_y$ alloy is believed to be the active catalyst (FIG. 15). The stability of the PtCo/SiO$_2$ alloy catalyst was also tested at high propane conversion at 500° C. It should be noted that the equilibrium propane conversion for 2.3% C$_3$H$_8$/Ar at 500° C. is ~30%. As shown in FIG. 15, starting from equilibrium conversion, the propane conversion dropped in the first ~10 hours on stream, and leveled off at ~10% conversion. In the 20 hour test, no big further deactivation was observed.

c. Production of C$_2$ and C$_2$+ Alkanes on Non-oxidative CH$_4$ Coupling Catalysts.

In one embodiment, the bimetallic catalyst may not be the catalyst but rather a different active species provides catalytic activity in conjunction. Without being bound by theory, it is hypothesized that the Pt and oxidized Mo sites (whether the Pt is a Mo alloy or not) work synergistically to convert the methane to a metal-bound species that can be further converted to the C2 and C3 products.

All the SiO$_2$-supported bi-metallic catalysts were synthesized using a sequential grafting method. Mo was firstly grafted onto the SiO$_2$ surface using the incipient wetness impregnation MD method. After the SiO$_2$-supported Mo was calcined, Pt precursor was impregnated onto the SiO$_2$ surface. Reduction with H$_2$ at high temperature leads to the generation of the active catalyst. Detailed synthesis of the catalyst is shown below using the 0.2 wt % Pt 2 wt % Mo/SiO$_2$ as an example. 0.92 g of (NH$_4$)$_6$Mo$_7$O$_{24}$.4H$_2$O was dissolved in 50 mL of DI H$_2$O, and concentrated NH$_4$OH was added to adjust the pH to 10. 25 mL of the Mo solution was impregnated onto 25.0 g of silica (Davisil 646, 35-60 mesh, 300 m$^2$/g and 1.1 cm$^3$/g, Aldrich). After drying at 120° C. for 1 hour, the Mo/SiO$_2$ was calcined by ramping over 2 h to 650° C. and holding for 6 h. Pt was grafted by impregnating Pt(NH$_3$)$_4$(NO$_3$)$_2$ aqueous solution onto the Mo/SiO$_2$. Pt(NH$_3$)$_4$(NO$_3$)$_2$ solution (0.01 M, 1.0 mL) was impregnated onto the Mo/SiO$_2$ using the incipient wetness impregnation technique. After drying in air at 120° C., the catalyst was calcined in air at 650° C. for 6 hours before the NOCM test.

Catalyst testing was performed in a vertical, ⅜" quartz tube reactor equipped with gas flow meters and gas chromatography (GC) for product analysis. For each experiment, a specified amount of catalyst was supported on quartz wool within the quartz tube. Initially, the catalyst was flushed with Ar at 30 mL/min at room temperature, and then the temperature was ramped to 650° C. over 1 hour, and hold at 650° C. for 1 hour before switching the gas to Ar purging out the H$_2$. After the temperature is stable at the desired temperature (650° C. or 550° C.), the gas flow was switched to CH$_4$, and the product concentrations were analyzed by a flame ionization detector (FID) using H$_2$ (99.999%, Airgas USA, LLC) and air (<2 ppm H$_2$O, Airgas USA, LLC).

Figure 16A:
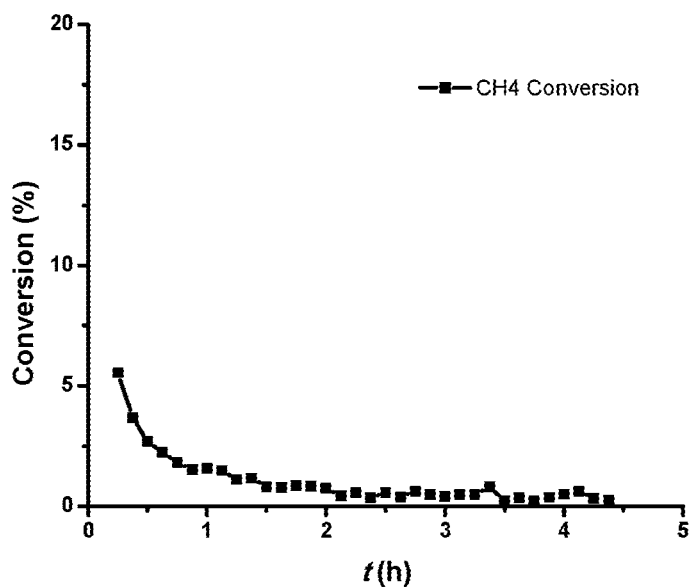
FIG. 16A is a plot of conversion for NOCM on 0.1 wt % Pt 2 wt % W/SiO$_2$.
Figure 16B:
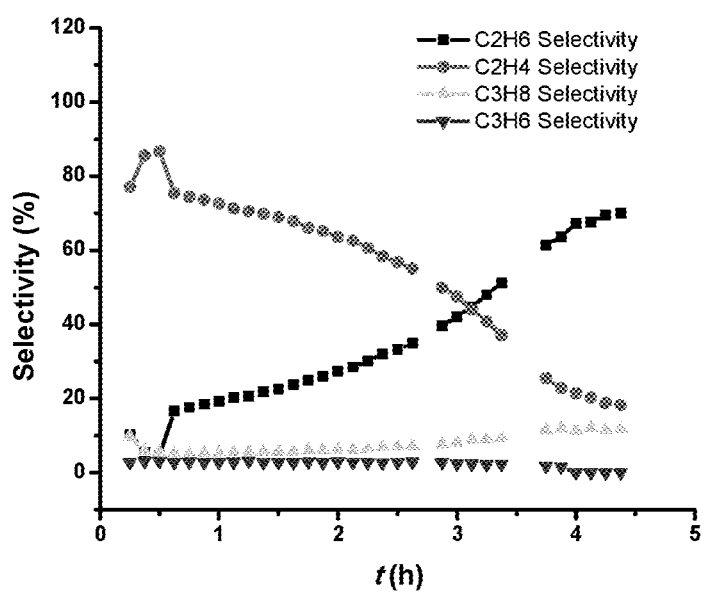
FIG. 16B is a plot of selectivity for NOCM on 0.1 wt % Pt 2% W/SiO$_2$ (300 mg of the 0.1% Pt 2% W/SiO$_2$ catalyst, 100% $CH_4$ with a flow rate of 5 mL/min, 650° C.).
Figure 17A:
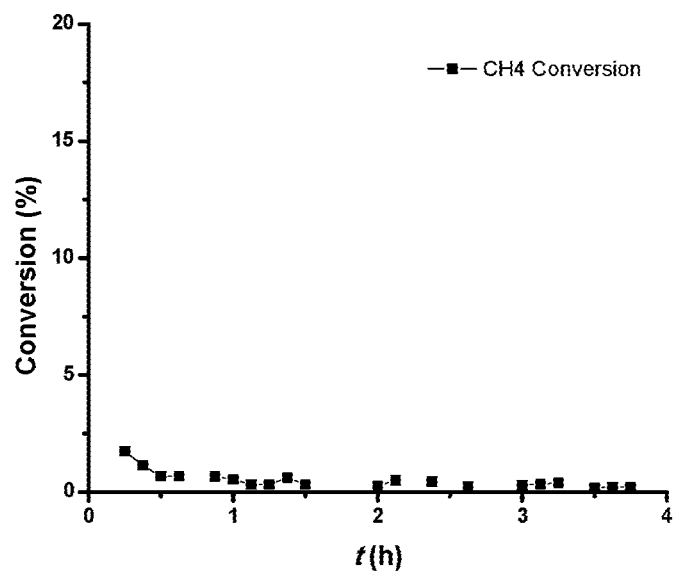
FIG. 17A is a plot of conversion for NOCM on 0.2 wt % Pt/SiO$_2$.
Figure 17B:
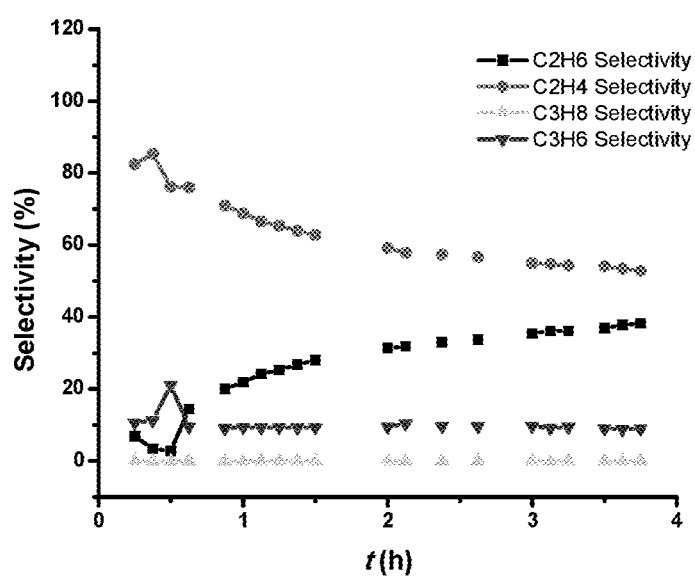
FIG. 17B is a plot of selectivity for NOCM on 0.2 wt % Pt/SiO$_2$ (300 mg of the 0.2% Pt/SiO$_2$ catalyst, 100% $CH_4$ with a flow rate of 5 mL/min, 650° C.).
Figure 18A:
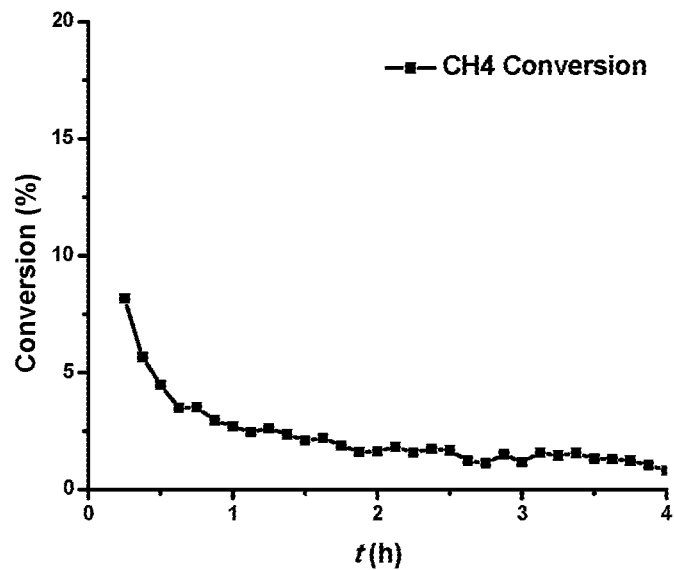
FIGS. 18A and 18B show data for NOCM on 0.1 wt % Pt 2 wt % Mo/SiO$_2$ 300 mg of the 0.1% Pt 2% W/SiO$_2$ catalyst, 650° C., 100% $CH_4$ with a flow rate of 5 mL/min.
Figure 18B:
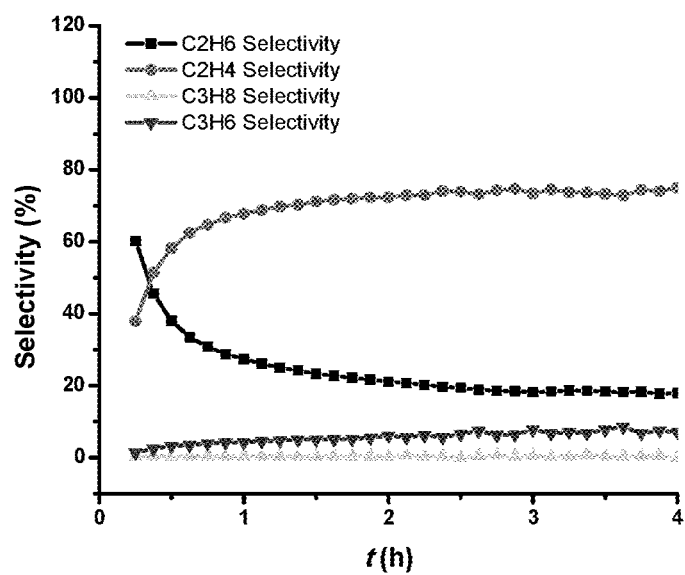
Figure 18C:
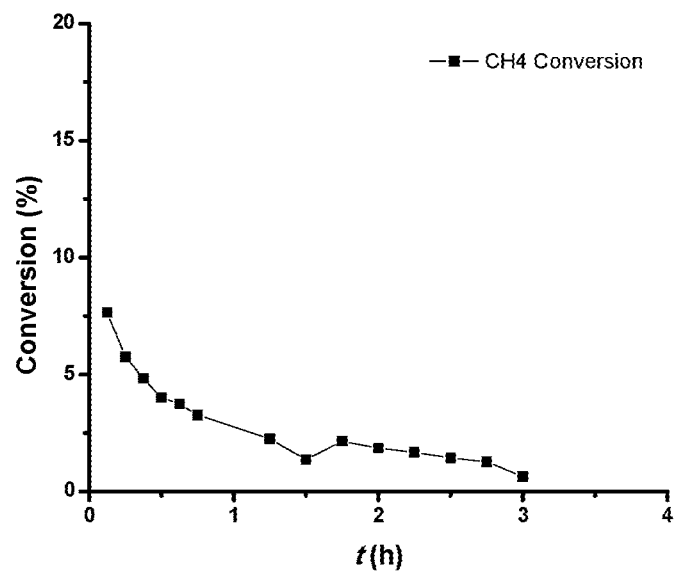
FIGS. 18C-18D show data for 300 mg of the 0.1% Pt 2% W/SiO$_2$ catalyst, 650° C., 100% $CH_4$ with a flow rate of 12 mL/min.
Figure 18D:
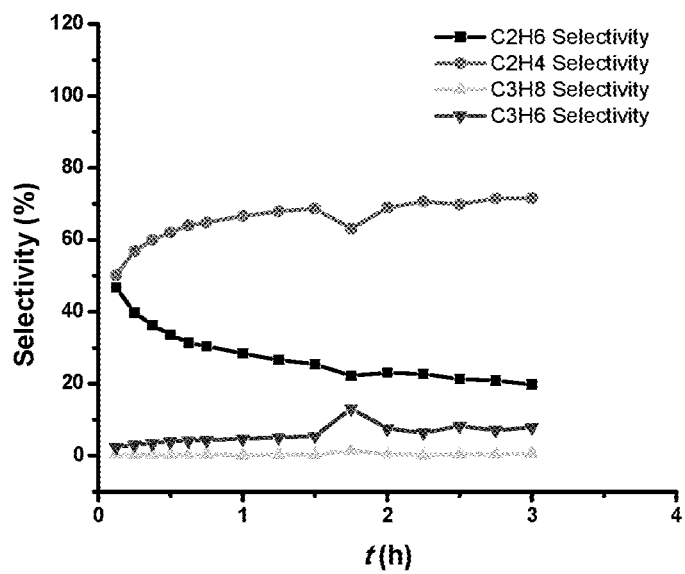

The NOCM results of PtW/SiO$_2$ catalyst are shown in FIG. 16. The initial CH4 conversion reaches 6%, and the conversion went down in the 4-hour test. The initial C$_2$H$_4$ selectivity is about 80%, and C$_2$H$_6$ selectivity is about 20%. After 4 hours on stream, the C$_2$H$_4$ selectivity dropped to about 20%, while the C$_2$H$_6$ selectivity increased to about 70%, with about 10% $C_3H_6$ selectivity. Compared with 0.2 wt % $Pt/SiO_2$ catalyst (shown in FIG. 17), the $PtW/SiO_2$ catalyst gave higher $CH_4$ conversion and longer lifetime. $PtMo/SiO_2$ catalyst gave higher $CH_4$ initial conversion (~8%), and the conversion remained higher than 1% after 4 hours on stream (better stability than $Pt/SiO_2$ and $PtW/SiO_2$ catalysts). In the 4-hour test, the $C_2H_6$ selectivity increased from ~40% to 70%, while the $C_2H_4$ selectivity decreased from 60% to 20%. $C_3H_6$ selectivity increased to about 10% after 4 hours on stream.

Figure 19A:
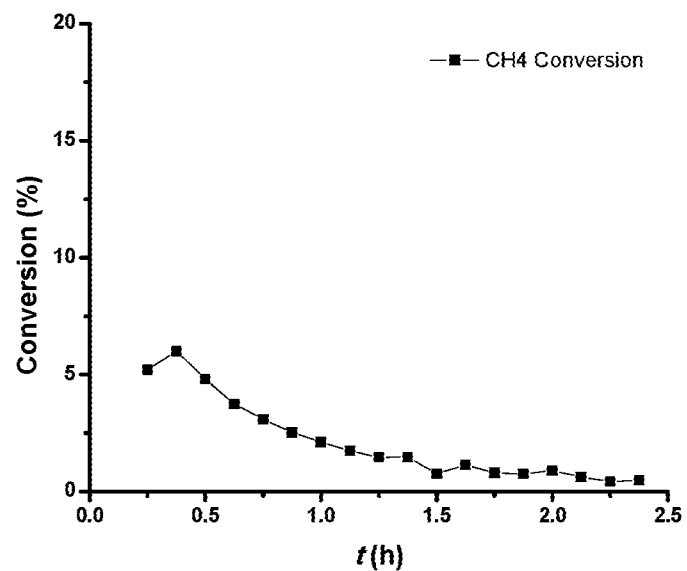
FIG. 19A is a plot of conversion.
Figure 19B:
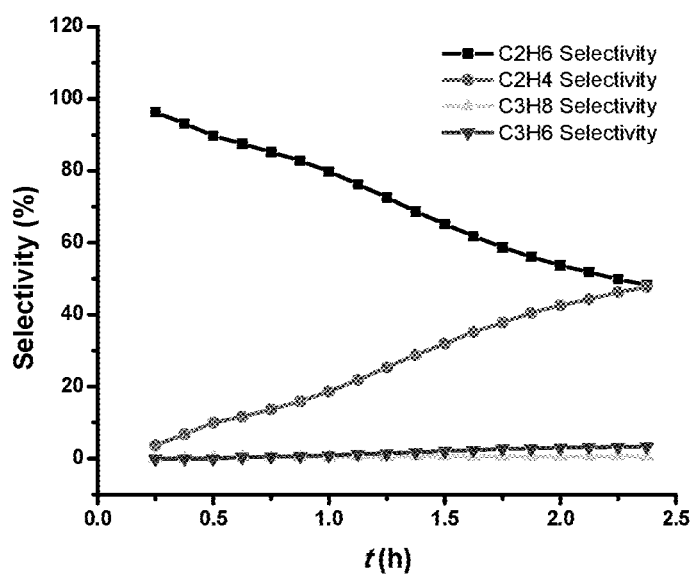
FIG. 19B is a plot for selectivity (NOCM on 0.1 wt % Pt 2 wt % Mo/SiO$_2$ 300 mg of the 0.1% Pt 2% Mo/SiO$_2$ catalyst, 550° C., 100% $CH_4$ with a flow rate of 12 mL/min).
Figure 20A:
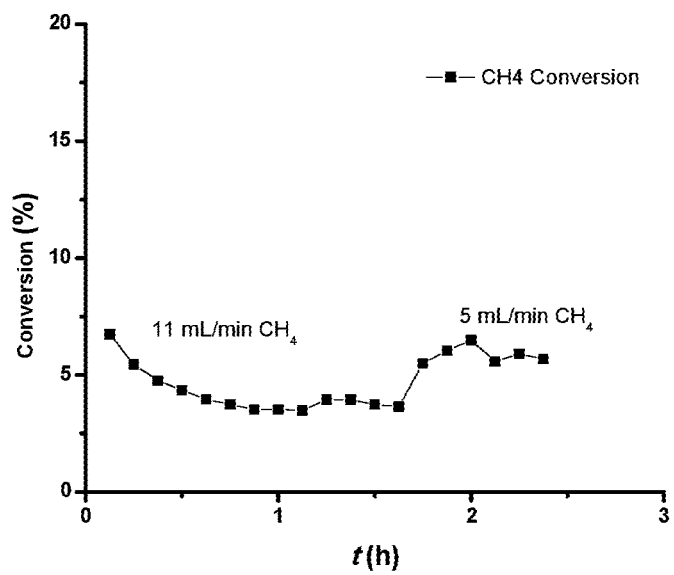
FIG. 20A is a plot of conversion and FIG. 20B is a plot for selectivity (PtMo/C alloy catalyst (NOCM 0.5 wt % Pt, Pt/Mo molar ratio 1/1, 300 mg of the PtMo/C catalyst, 650° C., 100% $CH_4$).
Figure 20B:
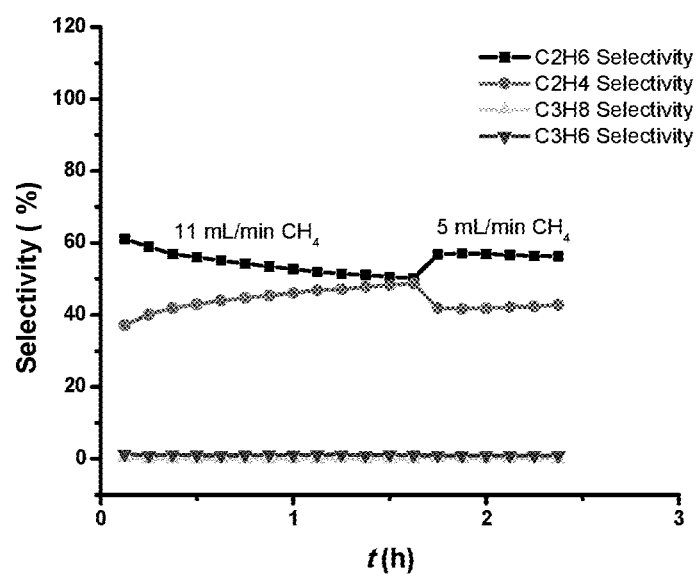

Doubling the $CH_4$ flow rate to 12 mL/min did not change the $CH_4$ conversion or the product selectivity, suggesting that under these reaction conditions, the reaction has reached the equilibrium, and higher rate could be achieved using higher $CH_4$ flow rate. As shown in FIGS. 19A-B, decreasing the reaction temperature to 550° C. led to lower conversion (~5% initially). The gas product selectivity started with ~90% $C_2H_6$ and 10% $C_2H_4$, and after 3 hours on stream, the $C_2H_4$ selectivity increased to ~50%, while $C_2H_6$ selectivity decreased to ~50%.

As a comparison, carbon supported PtMo alloy catalyst was synthesized and tested in the NOCM reaction. As shown in FIG. 5, PtMo/C is also active for NOCM reaction, but it gave a different product selectivity from the $PtMo/SiO_2$ catalyst. $C_2H_4$ selectivity is ~60%, while the $C_2H_6$ selectivity is ~40%. The results suggest that the active species in the $PtMo/SiO_2$ catalyst might not be PtMo alloy, although the alloy is also active for NOCM reaction.

Figure 21A:
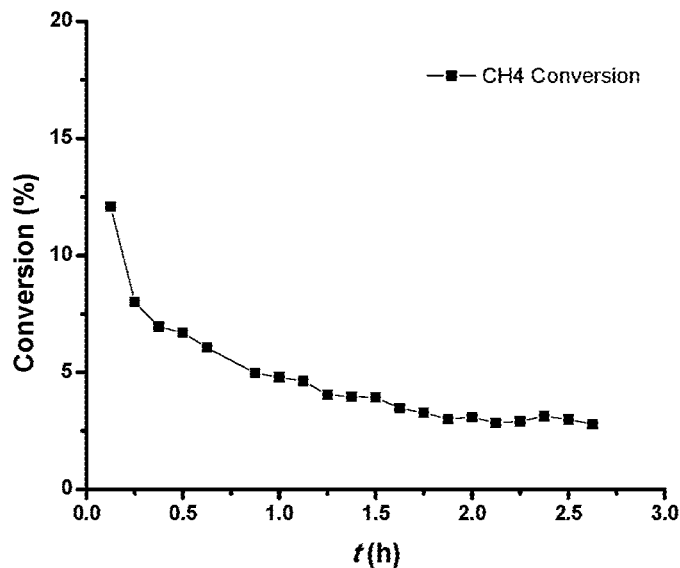
FIG. 21A is s a plot of conversion and FIG. 21B is a plot for selectivity (NOCM RuMo/SiO$_2$ catalyst 300 mg of the 0.2% Ru 2% Mo/SiO$_2$ catalyst, 650° C., 100% $CH_4$ with a flow rate of 12 mL/min).
Figure 21B:
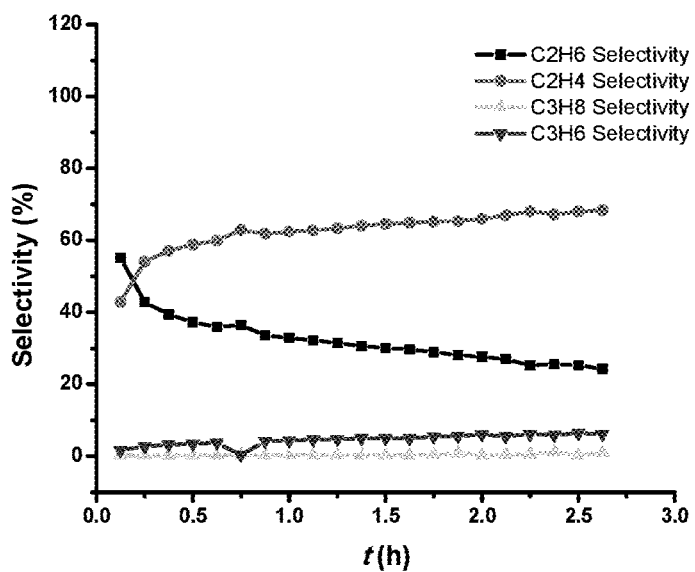
Figure 22A:
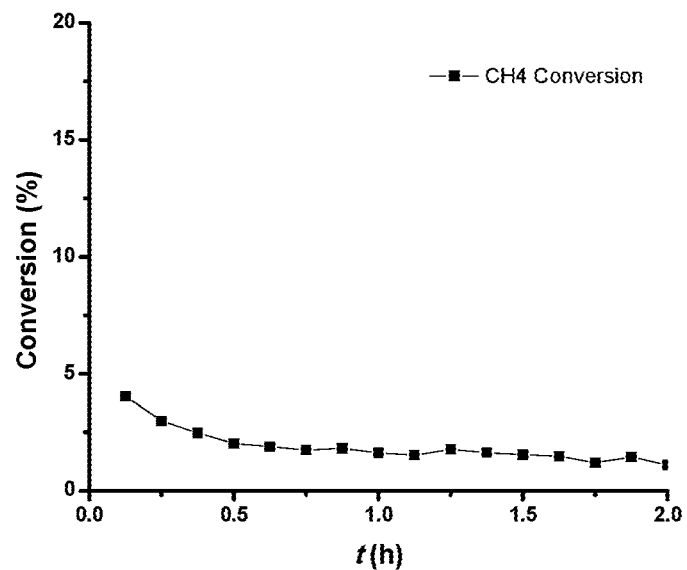
FIG. 22A is a plot of conversion and FIG. 22B is a plot for selectivity (NOCM RhMo/SiO$_2$ catalyst 300 mg of the 0.2% Rh 2% Mo/SiO$_2$ catalyst, 650° C., 100% $CH_4$ with a flow rate of 12 mL/min).
Figure 22B:
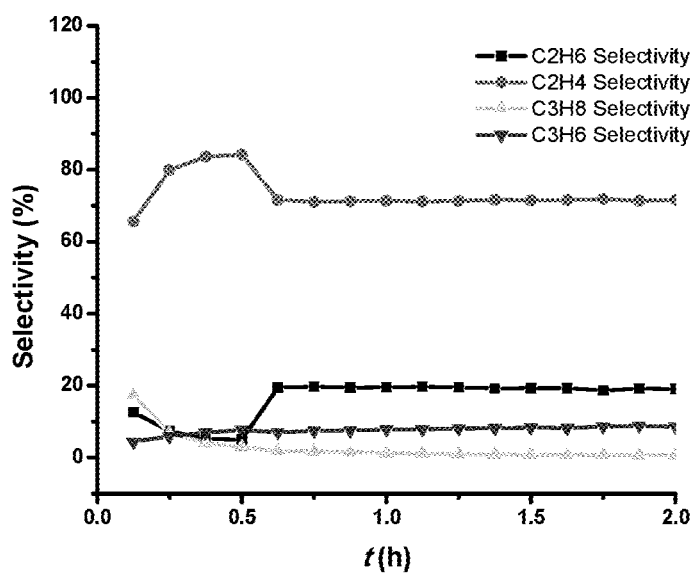

0.2% Ru 2% $Mo/SiO_2$ and 0.2% Ir 2% $Mo/SiO_2$ are also active for NOCM reaction, and $RuMo/SiO_2$ gave higher $CH_4$ conversion, but both catalysts gave similar gas phase product selectivity, ~70% $C_2H_4$, ~20% $C_2H_6$ and ~10% $C_3H_6$, as shown in FIGS. 21 and 22.

1) Definitions

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A catalytic article of manufacture comprising:
    a support comprising a perovskite having the composition $La_xSr_{1-x}Cr_yFe_{1-y}O_3$ where x is greater than 0 and less than 1, y is 0.3 to 0.7; and
    a metallic catalyst selected from the group consisting of metallic and bi-metallic catalysts.

2. The catalytic article of manufacture of claim 1, wherein the support comprises a perovskite and wherein x is 0.3 to 0.7.

3. The catalytic article of manufacture of claim 2, wherein metallic catalyst is a single metal catalyst.

4. The catalytic article of manufacture of claim 1, wherein the support comprises a perovskite and wherein x is 0.75 and y is 0.7.

5. The catalytic article of manufacture of claim 4, wherein the single metal catalyst is selected from the group consisting of Mo, Co, and Ce.

6. The catalytic article of manufacture of claim 1, wherein the support comprises a perovskite and wherein y is 0.5.

7. The catalytic article of manufacture of claim 1, wherein the metallic catalyst is Ce and further wherein the metallic catalyst is doped within the perovskite of the support.

8. The catalytic article of manufacture of claim 1, wherein the support comprises a fluorite and wherein z is 0.1.

9. The catalytic article of manufacture of claim 1 wherein the metallic catalyst is a bimetallic catalyst.

10. The catalytic article of manufacture of claim 9, wherein the bimetallic catalyst comprises Pt as a first metal.

11. The catalytic article of manufacture of claim 10, wherein a second metal of the bimetallic catalyst is selected from the group comprising Re, Co, and Ga.

* * * * *